United States Patent
Kermani et al.

(10) Patent No.: US 10,130,808 B2
(45) Date of Patent: Nov. 20, 2018

(54) SYSTEM AND METHOD FOR PROVIDING IONTOPHORESIS AT TYMPANIC MEMBRANE

(71) Applicant: Tusker Medical, Inc., Menlo Park, CA (US)

(72) Inventors: Mahyar Z. Kermani, San Ramon, CA (US); Bernard H. Andreas, Redwood City, CA (US); Rohit Girotra, Mountain View, CA (US); Mansour A. Saleki, San Jose, CA (US); Nikhil D. Bhat, Fremont, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 820 days.

(21) Appl. No.: 13/804,491

(22) Filed: Mar. 14, 2013

(65) Prior Publication Data

US 2014/0276352 A1    Sep. 18, 2014

(51) Int. Cl.
*A61N 1/30* (2006.01)
*A61F 11/00* (2006.01)
(Continued)

(52) U.S. Cl.
CPC ............... *A61N 1/30* (2013.01); *A61F 11/00* (2013.01); *A61F 11/002* (2013.01);
(Continued)

(58) Field of Classification Search
CPC ...... A61N 1/30; A61N 1/0428; A61N 1/0472; A61N 1/0526; A61N 1/303; A61N 1/306;
(Continued)

(56) References Cited

U.S. PATENT DOCUMENTS

| | | |
|---|---|---|
| 858,673 A | 7/1907 | Roswell |
| 1,920,006 A | 7/1933 | Dozier et al. |

(Continued)

FOREIGN PATENT DOCUMENTS

| | | |
|---|---|---|
| CN | 86105171 A | 3/1987 |
| CN | 2087067 U | 10/1991 |

(Continued)

OTHER PUBLICATIONS

U.S. Appl. No. 13/804,553, filed Mar. 14, 2013.
(Continued)

*Primary Examiner* — Nathan R Price
*Assistant Examiner* — Justin L Zamory

(57) ABSTRACT

Various systems and methods provide iontophoretic delivery of anesthesia at a patient's tympanic membrane. Some implementations provide channel switching enabling a single current sink to pull current through two electrodes in an alternating fashion based on clock pulses. The iontophoretic delivery of anesthesia may be driven by an AC modulated current. Some implementations provide for continuous flow of fresh iontophoresis fluid to the ear canal during iontophoresis. The fluid flows from a source reservoir into the cavity between the tympanic membrane and a plug, and then drains out of the cavity to a reservoir. An iontophoresis system may also detect capacitance between an anode electrode and an auxiliary electrode in a patient's ear canal, watching for reduced capacitance to indicate presence of a bubble in the iontophoresis fluid.

20 Claims, 23 Drawing Sheets

(51) Int. Cl.
*A61N 1/32* (2006.01)
*A61N 1/04* (2006.01)
*A61N 1/05* (2006.01)

(52) U.S. Cl.
CPC ......... *A61N 1/0428* (2013.01); *A61N 1/0472* (2013.01); *A61N 1/303* (2013.01); *A61N 1/325* (2013.01); *A61N 1/0526* (2013.01); *A61N 1/306* (2013.01)

(58) Field of Classification Search
CPC ..... A61N 1/325; A61F 11/002; A61K 9/0009; A61K 9/0046
See application file for complete search history.

(56) References Cited

U.S. PATENT DOCUMENTS

| | | | |
|---|---|---|---|
| 2,458,884 A | 1/1949 | Volkmann | |
| 3,741,197 A | 6/1973 | Sanz et al. | |
| 3,888,258 A | 6/1975 | Akiyama | |
| 3,897,786 A | 8/1975 | Garnett et al. | |
| 3,913,584 A | 10/1975 | Walchle et al. | |
| 3,948,271 A | 4/1976 | Akiyama | |
| 3,991,755 A | 11/1976 | Vernon et al. | |
| 4,149,533 A * | 4/1979 | Ishikawa | A61C 19/06 604/20 |
| 4,206,756 A | 6/1980 | Grossan | |
| 4,406,282 A | 9/1983 | Parker et al. | |
| 4,468,218 A | 8/1984 | Armstrong | |
| 4,473,073 A | 9/1984 | Darnell | |
| 4,552,137 A | 11/1985 | Strauss | |
| 4,564,009 A | 1/1986 | Brinkhoff | |
| 4,601,294 A | 7/1986 | Danby et al. | |
| 4,712,537 A | 12/1987 | Pender | |
| 4,968,296 A | 11/1990 | Ritch et al. | |
| 4,971,076 A | 11/1990 | Densert et al. | |
| 5,026,378 A | 6/1991 | Goldsmith, III | |
| 5,044,373 A | 9/1991 | Northeved et al. | |
| 5,047,007 A | 9/1991 | McNichols et al. | |
| 5,053,040 A | 10/1991 | Goldsmith, III | |
| 5,107,861 A | 4/1992 | Narboni | |
| 5,135,478 A | 8/1992 | Sibalis | |
| 5,160,316 A | 11/1992 | Henley | |
| 5,254,081 A * | 10/1993 | Maurer | A61N 1/30 128/898 |
| 5,254,120 A | 10/1993 | Cinberg et al. | |
| 5,261,903 A | 11/1993 | Dhaliwal et al. | |
| D352,780 S | 11/1994 | Glaeser et al. | |
| 5,421,818 A | 6/1995 | Arenberg | |
| 5,466,239 A | 11/1995 | Cinberg et al. | |
| 5,496,329 A | 3/1996 | Reisinger | |
| D378,611 S | 3/1997 | Croley | |
| 5,610,988 A | 3/1997 | Miyahara | |
| 5,643,280 A | 7/1997 | Del Rio et al. | |
| 5,674,196 A | 10/1997 | Donaldson et al. | |
| D387,863 S | 12/1997 | Herman et al. | |
| 5,707,383 A | 1/1998 | Bays et al. | |
| 5,792,100 A | 8/1998 | Shantha | |
| 5,804,957 A * | 9/1998 | Coln | A61N 1/0432 323/282 |
| 5,827,295 A | 10/1998 | Del Rio et al. | |
| 5,893,828 A | 4/1999 | Uram | |
| 5,979,072 A | 11/1999 | Collins, II | |
| D418,223 S | 12/1999 | Phipps et al. | |
| D420,741 S | 2/2000 | Croley | |
| 6,045,528 A | 4/2000 | Arenberg et al. | |
| D424,197 S | 5/2000 | Sydlowski et al. | |
| 6,059,803 A | 5/2000 | Spilman | |
| D426,135 S | 6/2000 | Lee | |
| 6,137,889 A | 10/2000 | Shennib et al. | |
| 6,148,821 A | 11/2000 | Falco et al. | |
| 6,183,469 B1 | 2/2001 | Thapliyal et al. | |
| 6,200,280 B1 | 3/2001 | Brenneman et al. | |
| 6,206,888 B1 | 3/2001 | Bicek et al. | |
| 6,245,077 B1 | 6/2001 | East et al. | |
| 6,251,121 B1 | 6/2001 | Saadat | |
| 6,295,469 B1 | 9/2001 | Linkwitz et al. | |
| D450,843 S | 11/2001 | McGuckin, Jr. et al. | |
| 6,347,246 B1 | 2/2002 | Perrault et al. | |
| 6,358,231 B1 | 3/2002 | Schindler et al. | |
| 6,440,102 B1 | 8/2002 | Arenberg et al. | |
| 6,475,138 B1 | 11/2002 | Schechter et al. | |
| 6,512,950 B2 | 1/2003 | Li et al. | |
| 6,514,261 B1 | 2/2003 | Randall et al. | |
| 6,520,939 B2 | 2/2003 | Lafontaine | |
| 6,522,827 B1 | 2/2003 | Loeb et al. | |
| 6,553,253 B1 | 4/2003 | Chang | |
| 6,640,121 B1 | 10/2003 | Telischi et al. | |
| 6,645,173 B1 | 11/2003 | Liebowitz | |
| 6,648,873 B2 | 11/2003 | Arenberg et al. | |
| 6,663,575 B2 | 12/2003 | Leysieffer | |
| 6,682,558 B2 | 1/2004 | Tu et al. | |
| 6,770,080 B2 | 8/2004 | Kaplan et al. | |
| 6,916,159 B2 | 7/2005 | Rush et al. | |
| 7,123,957 B2 | 10/2006 | Avrahami | |
| 7,127,285 B2 | 10/2006 | Henley et al. | |
| 7,137,975 B2 | 11/2006 | Miller et al. | |
| D535,027 S | 1/2007 | James et al. | |
| 7,160,274 B2 | 1/2007 | Ciok et al. | |
| 7,344,507 B2 | 3/2008 | Briggs et al. | |
| 7,351,246 B2 | 4/2008 | Epley | |
| 7,381,210 B2 | 6/2008 | Zarbatany et al. | |
| D595,410 S | 6/2009 | Luzon | |
| 7,563,232 B2 | 7/2009 | Freeman et al. | |
| D598,543 S | 8/2009 | Vogel et al. | |
| 7,654,997 B2 | 2/2010 | Makower et al. | |
| 7,677,734 B2 | 3/2010 | Wallace | |
| 7,704,259 B2 | 4/2010 | Kaplan et al. | |
| 7,749,254 B2 | 7/2010 | Sobelman et al. | |
| D622,842 S | 8/2010 | Benoist | |
| 8,052,693 B2 | 11/2011 | Shahoian | |
| 8,192,420 B2 | 6/2012 | Morriss et al. | |
| 8,249,700 B2 | 8/2012 | Clifford et al. | |
| 8,409,175 B2 | 4/2013 | Lee et al. | |
| 8,425,488 B2 | 4/2013 | Clifford et al. | |
| 8,452,392 B2 | 5/2013 | Morriss et al. | |
| 8,498,475 B2 | 7/2013 | Graylin | |
| 8,518,098 B2 | 8/2013 | Roeder et al. | |
| 8,702,722 B2 | 4/2014 | Shahoian | |
| 8,840,802 B2 | 9/2014 | Morriss et al. | |
| 8,849,394 B2 | 9/2014 | Clifford et al. | |
| 9,011,363 B2 | 4/2015 | Clopp et al. | |
| 9,023,059 B2 | 5/2015 | Loushin et al. | |
| 9,216,112 B2 | 12/2015 | Clifford et al. | |
| 9,364,648 B2 | 6/2016 | Girotra et al. | |
| 9,387,124 B2 | 7/2016 | Clifford | |
| 9,392,229 B2 | 7/2016 | Morriss et al. | |
| 9,707,131 B2 | 7/2017 | Shahoian | |
| 9,713,710 B2 | 7/2017 | Morriss et al. | |
| 2002/0026125 A1 | 2/2002 | Leysieffer | |
| 2002/0069383 A1 | 6/2002 | Hirchenbain | |
| 2002/0111585 A1 | 8/2002 | Lafontaine | |
| 2002/0138091 A1 | 9/2002 | Pflueger | |
| 2002/0161379 A1 | 10/2002 | Kaplan et al. | |
| 2002/0169456 A1 | 11/2002 | Tu et al. | |
| 2003/0060799 A1 | 3/2003 | Arenberg et al. | |
| 2003/0093057 A1 | 5/2003 | Zhang et al. | |
| 2003/0199791 A1 | 10/2003 | Boecker et al. | |
| 2004/0054339 A1 | 3/2004 | Ciok et al. | |
| 2005/0094335 A1 | 5/2005 | Doty | |
| 2005/0154357 A1 | 7/2005 | Pinel | |
| 2005/0182385 A1 | 8/2005 | Epley | |
| 2005/0235422 A1 | 10/2005 | Wallace | |
| 2005/0240147 A1 | 10/2005 | Makower et al. | |
| 2006/0142700 A1 | 6/2006 | Sobelman et al. | |
| 2006/0155304 A1 | 7/2006 | Kaplan et al. | |
| 2006/0177080 A1 | 8/2006 | Smith | |
| 2007/0003096 A1 | 1/2007 | Nam | |
| 2007/0078372 A1 | 4/2007 | Reddy et al. | |
| 2007/0183613 A1 | 8/2007 | Juneau et al. | |
| 2007/0233222 A1 | 10/2007 | Roeder et al. | |
| 2008/0011308 A1 | 1/2008 | Fleming | |
| 2008/0051804 A1 | 2/2008 | Cottler et al. | |
| 2008/0058756 A1 | 3/2008 | Smith | |

(56) References Cited

U.S. PATENT DOCUMENTS

| | | |
|---|---|---|
| 2008/0065002 A1 | 3/2008 | Lobl et al. |
| 2008/0107287 A1 | 5/2008 | Beard |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163848 A1* | 6/2009 | Morriss .............. A61F 11/00 604/20 |
| 2009/0209972 A1 | 8/2009 | Loushin et al. |
| 2009/0262510 A1 | 10/2009 | Pekkarinen et al. |
| 2009/0270807 A1 | 10/2009 | Mas et al. |
| 2009/0299344 A1 | 12/2009 | Lee et al. |
| 2010/0030131 A1 | 2/2010 | Morriss et al. |
| 2010/0041447 A1 | 2/2010 | Graylin |
| 2010/0061581 A1 | 3/2010 | Soetejo et al. |
| 2010/0198135 A1* | 8/2010 | Morriss .............. A61F 11/00 604/21 |
| 2010/0300460 A1 | 12/2010 | Falco et al. |
| 2011/0001564 A1 | 1/2011 | Hori |
| 2011/0015645 A1 | 1/2011 | Liu et al. |
| 2011/0048414 A1 | 3/2011 | Hoekman et al. |
| 2011/0268303 A1 | 11/2011 | Ahsani |
| 2011/0288559 A1 | 11/2011 | Shahoian |
| 2012/0310145 A1 | 12/2012 | Clifford et al. |
| 2013/0090544 A1 | 4/2013 | Clifford et al. |
| 2013/0190678 A1 | 7/2013 | Andreas et al. |
| 2013/0197426 A1 | 8/2013 | Morriss et al. |
| 2013/0223702 A1 | 8/2013 | Holsing et al. |
| 2014/0102461 A1 | 4/2014 | Girotra et al. |
| 2014/0194891 A1 | 7/2014 | Shahoian |
| 2014/0276906 A1 | 9/2014 | Andreas et al. |
| 2015/0068539 A1 | 3/2015 | Morriss et al. |
| 2016/0361204 A1 | 12/2016 | Girotra et al. |
| 2016/0375204 A1 | 12/2016 | Andreas et al. |
| 2017/0014272 A1 | 1/2017 | Ray et al. |
| 2017/0028193 A1 | 2/2017 | Morriss et al. |

FOREIGN PATENT DOCUMENTS

| | | |
|---|---|---|
| CN | 2409940 Y | 12/2000 |
| DE | 19618585 | 11/1997 |
| EP | 0214527 A1 | 3/1987 |
| FR | 2526656 | 11/1983 |
| JP | S59-129815 | 8/1984 |
| JP | H 07-116190 A | 5/1995 |
| JP | 2010-524584 | 7/2010 |
| WO | WO 92/10223 | 6/1992 |
| WO | WO 2002/043795 | 6/2002 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2010/014894 | 2/2010 |
| WO | WO 2011/081772 | 7/2011 |
| WO | WO 2013/016098 | 1/2013 |
| WO | WO 2013/181009 | 12/2013 |
| WO | WO 2014/158543 | 10/2014 |
| WO | WO 2017/011777 | 1/2017 |

OTHER PUBLICATIONS

U.S. Appl. No. 60/912,902, filed Apr. 19, 207.
Patent Examination Report No. 1 for Australian Patent Application No. 2008242735, dated Aug. 8, 2012, 3 pages.
Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, dated Sep. 3, 2008.
Written Opinion for International Application No. PCT/US2008/060779, dated Sep. 3, 2008.
Office Action for U.S. Appl. No. 11/749,733, dated Jun. 10, 2009, 13 pages.
Office Action for U.S. Appl. No. 11/749,733, dated Dec. 2, 2008, 9 pages.
U.S. Appl. No. 61/085,360, filed Jul. 31, 2008.
Patent Examination Report No. 1 for Australian Application No. 2009276384, dated Apr. 14, 2014, 3 pages.
Office Action for Canadian Application No. 2,732,595, dated Dec. 8, 2015, 4 pages.
Office Action for Russian Application No. 2011-07228, dated May 24, 2013.
International Search Report for International Application No. PCT/US2009/052395, dated Nov. 6, 2009.
Written Opinion for International Application No. PCT/US2009/052395, dated Nov. 6, 2009.
Patent Examination Report No. 1 for Australian Application No. 2010337214, dated Feb. 27, 2015, 3 pages.
Office Action for Chinese Application No. 201080065012.2, dated Mar. 31, 2016, 20 pages.
International Search Report for International Application No. PCT/US2010/058718, dated Feb. 17, 2011.
Written Opinion for International Application No. PCT/US2010/058718, dated Feb. 17, 2011.
International Search Report for International Application No. PCT/US2010/042128, dated Aug. 27, 2010.
Office Action for Australian Application No. 2012287268, dated Feb. 11, 2016.
Office Action for European Application No. 12743007.2, dated Jul. 21, 2016, 5 pages.
Notification of Reasons for Refusal for Japanese Application No. 2014-522882, dated May 31, 2016, English Translation.
International Search Report for International Application No. PCT/US2012/047179, dated Mar. 11, 2013.
Written Opinion for International Application No. PCT/US2012/047179, dated Mar. 11, 2013.
First Office Action for Chinese Patent Application No. 201380027926.3, dated May 3, 2016.
International Search Report for International Application No. PCT/US2013/041816, dated Sep. 16, 2013, 7 pages.
Written Opinion for International Application No. PCT/US2013/041816, dated Sep. 16, 2013, 7 pages.
International Search Report and Written Opinion for International Application No. PCT/US2014/018017, dated May 22, 2014, 12 pages.
International Search Report for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).

(56) References Cited

OTHER PUBLICATIONS

Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
International Search Report and Written Opinion for International Application No. PCT/US2016/042577, dated Dec. 6, 2016, 14 pages.

\* cited by examiner

SYSTEM AND METHOD FOR PROVIDING IONTOPHORESIS AT TYMPANIC MEMBRANE

BACKGROUND

Some children may exhibit recurrent episodes of otitis media and/or -otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012, the disclosure of which is incorporated by reference herein. Still additional exemplary pressure equalization tube delivery systems are disclosed in U.S. Pub. No. 2011/0015645, entitled "Tympanic Membrane Pressure Equalization Tube Delivery System," published Jan. 20, 2011, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
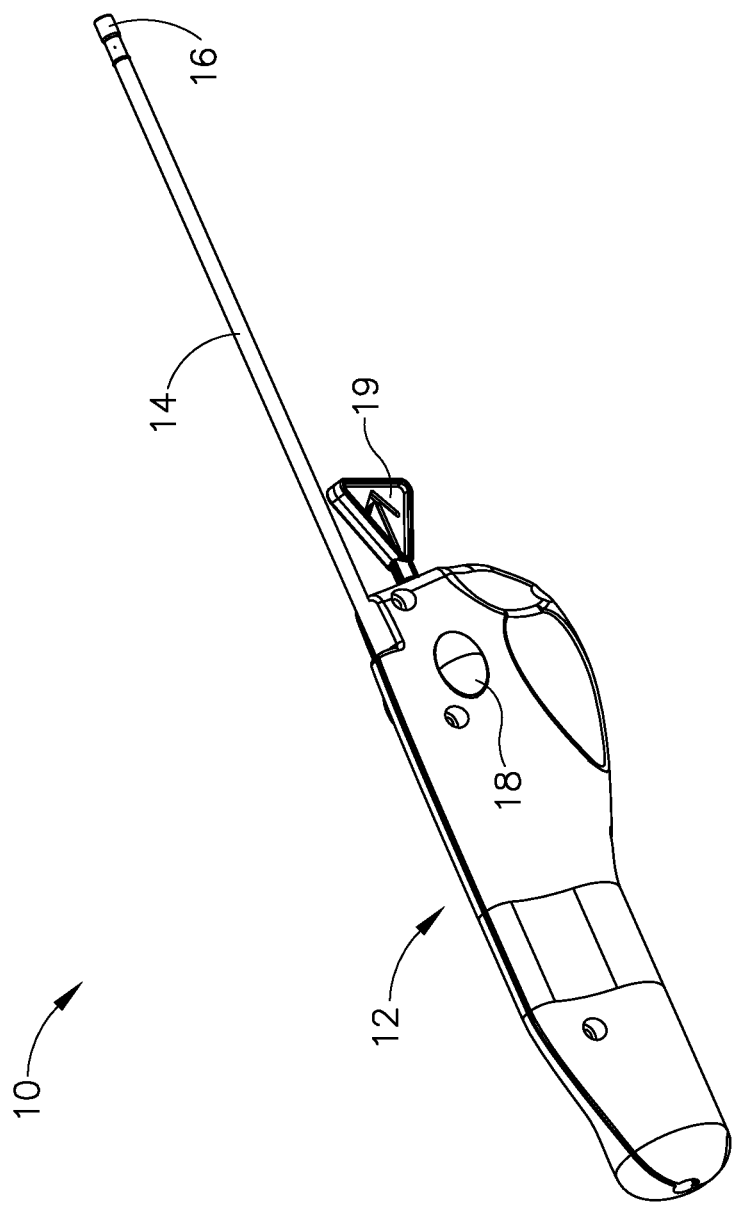
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Pressure Equalization Tube Delivery Device (PETDD)

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (10) that may be used in such procedures. It should be understood that PETDD (10) may be used with an endoscope to provide visualization of the tympanic membrane (TM) during use of PETDD (10). It should also be understood that a patient may receive local anesthesia at the tympanic membrane (TM) through a process of iontophoresis before PETDD (100) is actuated to deploy a PE tube. Various examples of devices and methods that may be used to provide iontophoresis will be described in greater detail below. It should also be understood that iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein.

As shown in FIG. 1, PETDD (10) of this example includes a handpiece (12) and a cannula (14) extending distally from handpiece (12). Cannula (14) is sized for insertion in a patient's ear canal, such that the tip (16) of cannula may directly engage the patient's tympanic membrane (TM). As soon as the tip (16) achieves apposition with the tympanic membrane (TM), the operator may depress button (18), which may trigger a firing sequence whereby PETDD (10) creates a myringotomy incision, dilates the myringotomy incision, and inserts a PE tube in the myringotomy incision nearly instantly. A pin (19) selectively locks button (18) to avoid premature firing of PETDD (10), such that the operator must remove pin (19) before intentionally firing PETDD (10). By way of example only, PETDD (10) may be constructed and operable in accordance with at least some of the teachings of U.S. Pat. No. 8,052,693, the disclosure of which is incorporated by reference herein; U.S. Pat. No. 8,249,700, the disclosure of which is incorporated by reference herein; U.S. Pub. No. 2011/0015645, the disclosure of which is incorporated by reference herein; and/or U.S. Pat. App. No. 13/804,553, entitled "Features to Improve and Sense Tympanic Membrane Apposition by Tympanostomy Tube Delivery Instrument," filed on Mar. 14, 2013, the disclosure of which is incorporated by reference herein. Other suitable forms that PETDD (10) may take will be apparent to those of ordinary skill in the art in view of the teachings herein. It should also be understood that a PE tube may be inserted in a tympanic membrane (TM) manually, such as by creating the myringotomy incision with a knife and inserting the PE tube using forceps, etc.

Figure 2:
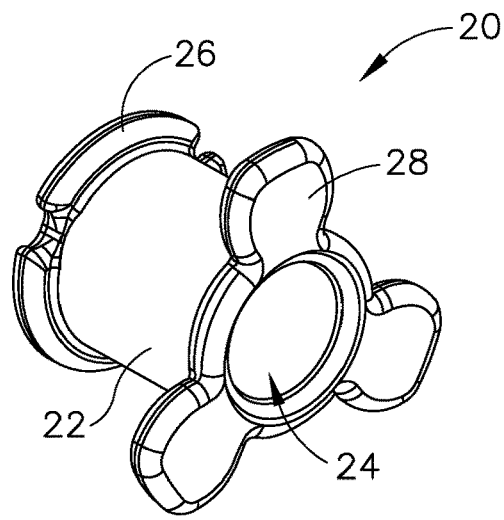
FIG. 2 depicts a perspective view of an exemplary pressure equalization (PE) tube suitable for delivery by the PETDD of FIG. 1.
Figure 3:
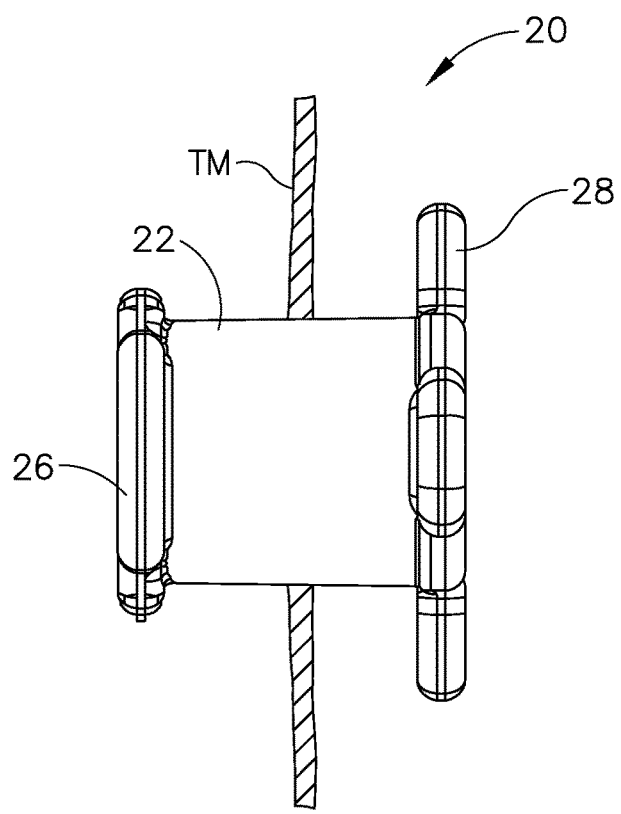
FIG. 3 depicts a side elevational view of the PE tube of FIG. 2, positioned within a tympanic membrane.

FIGS. 2-3 show an exemplary PE tube (20) that may be delivered to the tympanic membrane (TM) using PETDD (10). PE tube (20) of this example comprises a cylindraceous body (22) that defines a passageway (24). A flange (26) is located at one end of body (22) while a set of petals (28) are located at the other end of body (22). PE tube (20) is formed of a resilient material that is biased to assume the rivet like configuration shown in FIGS. 2-3. However, flange (26) and petals (28) may be flexed inwardly toward the longitudinal axis of body (22) to provide PE tube (20) with a cylindraceous configuration. In particular, flange (26) and petals (28) may be flexed such that their outer surfaces are at the same radial distance from the longitudinal axis as the outer perimeter of body (22). This may enable PE tube (200) to collapse to fit within cannula (14). When PE tube (20) is disposed in a tympanic membrane (TM), petals (28) are located medially (i.e., on the middle ear side) while flange (26) is located laterally (i.e., on the outer ear side). By way of example only, PE tube (20) may also be configured in accordance with at least some of the teachings of U.S. patent application Ser. No. 13/800,113, entitled "Tympanic Membrane Pressure Equalization Tube," filed on Mar. 13, 2013, the disclosure of which is incorporated by reference herein; and/or at least some of the teachings of U.S. Pat. App. No. 13/804,553, the disclosure of which is incorporated by reference herein. Other suitable forms that PE tube (20) may take will be apparent to those of ordinary skill in the art in view of the teachings herein.

II. Exemplary Iontophoresis System

As noted above, PETDD (10) may be used in conjunction with an iontophoresis system, which may be used to anesthetize the patient's ear before PETDD (10) is inserted into the patient's ear canal to deliver PE tube (20) in the tympanic membrane (TM). By way of example only, iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. In addition or in the alternative, iontophoresis may be provided in accordance with any of the various teachings below. It should be understood that any of the below teachings may be readily combined with at least some of the teachings of U.S. Pub. No. 2010/0198135, the disclosure of which is incorporated by reference herein; and/or at least some of the teachings of U.S. Pat. No. 8,192,420, the disclosure of which is incorporated by reference herein.

Figure 4:
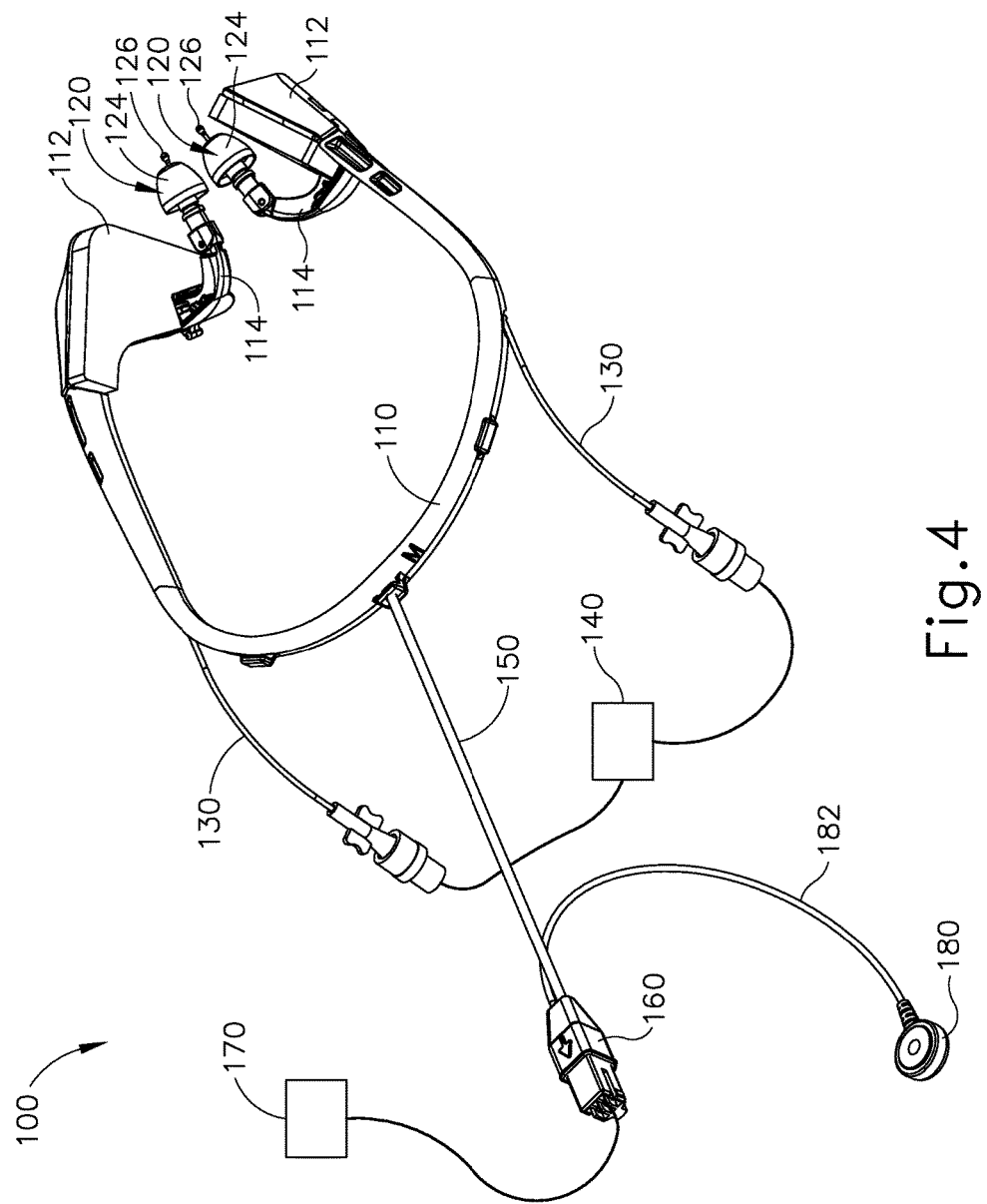
FIG. 4 depicts an exemplary iontophoresis system incorporating a headset.

FIG. 4 shows one merely illustrative iontophoresis system (100). Iontophoresis system (100) of this example comprises a headframe (110), a fluid source (140), and a control unit (170). Headframe (110) includes a pair of coupling features (112) that are pivotally coupled with arms (114). Each arm (114) has an associated earplug (120) pivotally coupled with the corresponding arm (114). Headframe (110) is formed of a resilient material enabling headframe (110) to accommodate patients with various head sizes. Pivoting of arms (114) at coupling features (112) and pivoting of earplugs (120) at arms (114) also facilitate fitting of earplugs (120) in the ears of patients having various head sizes. Coupling features (112) and/or arms (114) may also include torsion springs, ratcheting features, and/or various other features to provide stability once earplugs (120) have been suitably positioned for insertion in the patient's ears.

Each earplug (120) includes a flexible sealing element (124) and a distally projecting nozzle (126). Sealing element (124) is configured to provide a fluid tight seal against the patient's ear canal when earplug (120) is inserted in the patient's ear canal. Nozzle (126) is positioned to project into the patient's ear canal when earplug (120) is inserted in the patient's ear canal, such that nozzle (126) is spaced lateral to the tympanic membrane (TM). Each nozzle (126) is in fluid communication with a respective conduit (130). Conduits (130) extend around headframe (110) and are coupled with a fluid source (140). Fluid source (140) contains an iontophoresis solution, which has a positive charge. Various suitable formulations for an iontophoresis solution will be apparent to those of ordinary skill in the art in view of the teachings herein. It should also be understood that fluid source (140) may be configured to drive the iontophoresis solution through conduits (130) toward nozzles (126) in various ways. By way of example only, fluid source (140) may comprise a pump (e.g., a syringe, etc.). As another merely illustrative example, fluid source (140) may be positioned higher than the patient such that gravity pulls the iontophoresis solution from fluid source and thereby drives the iontophoresis solution to nozzles (126). Other suitable ways in which iontophoresis solution may be delivered to nozzles (126) will be apparent to those of ordinary skill in the art in view of the teachings herein. Once delivered through nozzles (126), the iontophoresis solution may circulate in the region within the ear canal between the end of earplug (120) and the tympanic membrane (TM).

Each earplug (120) of this example also includes a respective internal electrode (not shown) that is operable to receive a positive electrical voltage. The electrodes may be formed of silver, gold, and/or any other suitable conductor. The electrodes are in communication with a cable (150), which wraps around headframe (110) and is coupled with a plug (160). Plug (160) is configured for insertion in a corresponding socket in control unit (170). Control unit (170) is operable to energize the electrodes in earplugs (120) via plug (160) and cable (150), thereby providing a positive voltage to the electrodes. Various suitable components and configurations that may be incorporated into control unit (170) are described in greater detail below; while other components and configurations that may be incorporated into control unit (170) will be apparent to those of ordinary skill in the art in view of the teachings herein.

A ground pad (180) is also coupled with plug (160) via a ground cable (182). Ground pad (180) is in the form of a patch that is configured to engage exposed skin of the patient to provide an electrical ground return path. When the electrodes of earplugs (120) are activated by control unit (170), this drives the iontophoresis solution away from earplugs (120) since the electrodes and iontophoresis solution both have a positive charge. The electrodes of earplugs (120) and control unit (170) thus provide an electrorepulsive force to the iontophoresis solution ions. The electrodes of earplugs (120) serve as an anode and the patient's tissue serves as a cathode, due to engagement with ground pad (180). The electrorepulsive force provided through the electrodes drives the anesthetic of the iontophoresis solution ions into the tympanic membrane (TM), thereby anesthetizing the tympanic membrane (TM) and/or adjacent tissue within the ear canal for subsequent delivery of PE tube (20) into the tympanic membrane (TM). The current is regulated to be independent of the load resistance. The current is applied for a certain amount of time such that the total amount of charge is controlled.

Figure 5:
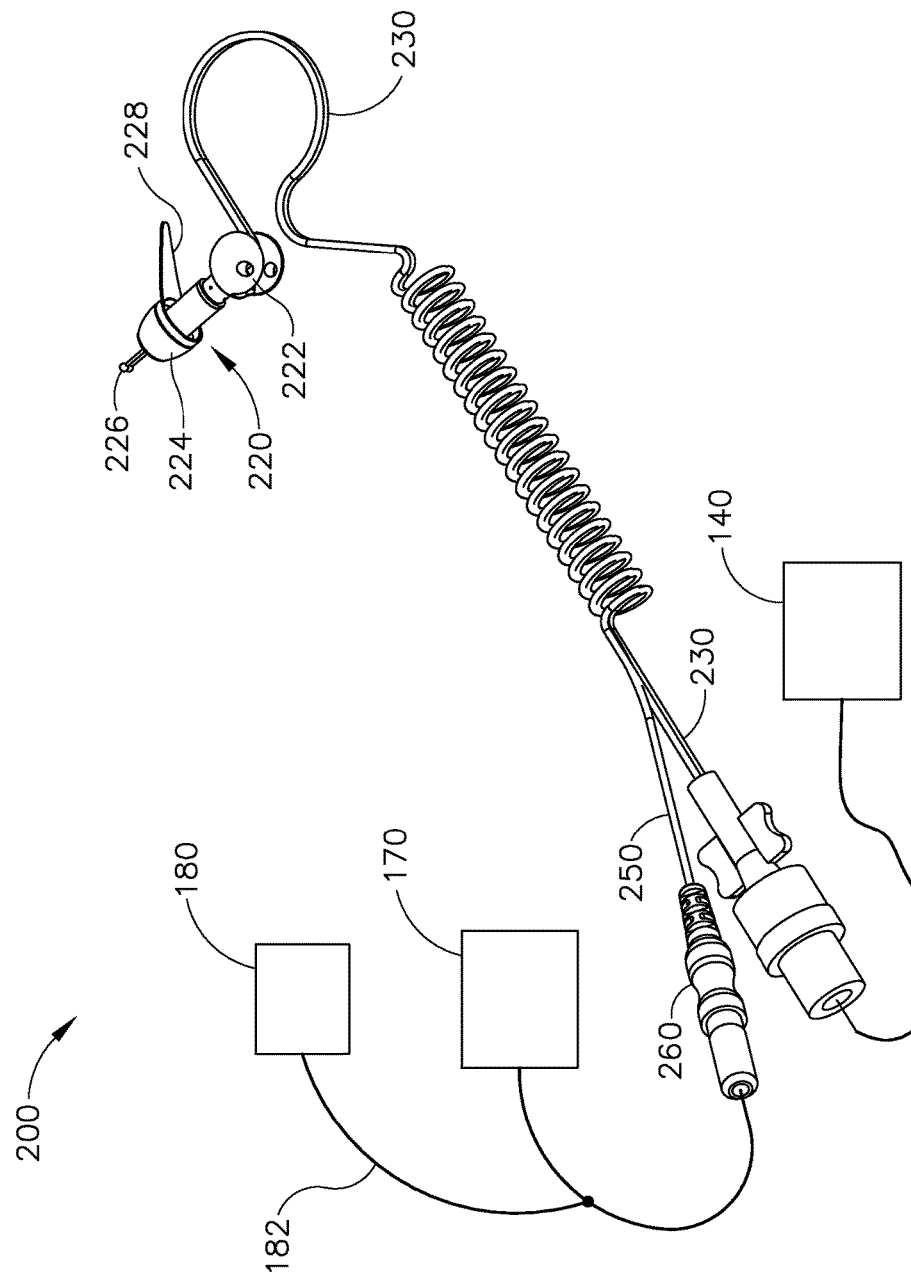
FIG. 5 depicts an exemplary alternative iontophoresis system incorporating an earplug.

FIG. 5 shows another merely illustrative iontophoresis system (200), which is substantially similar to iontophoresis system (100) except that iontophoresis system (200) does not have anything like headframe (110). Iontophoresis system (200) of this example comprises an earplug (220), fluid source (140), control unit (170), and ground pad (180). Earplug (220) is configured to be inserted into a patient's ear and remain there without needing a separate component like headframe (110) to hold it in place. By way of example only, a biocompatible adhesive may be used to assist in holding earplug (220) in place within a patient's ear canal. Earplug (220) includes a pair of gripping features (222) that are configured to be gripped and thereby serve as a handle during insertion of earplug (220) in a patient's ear. Earplug (220) also includes a pull-tab (228) that may be gripped and pulled to assist in removing earplug (220) from the patient's ear. Of course, these features are mere examples, and any other suitable kinds of gripping features may be incorporated into earplug (220). While only one earplug (220) is shown, it should be understood that iontophoresis system (200) may have two earplugs (220) that may be used simultaneously.

Figure 6:
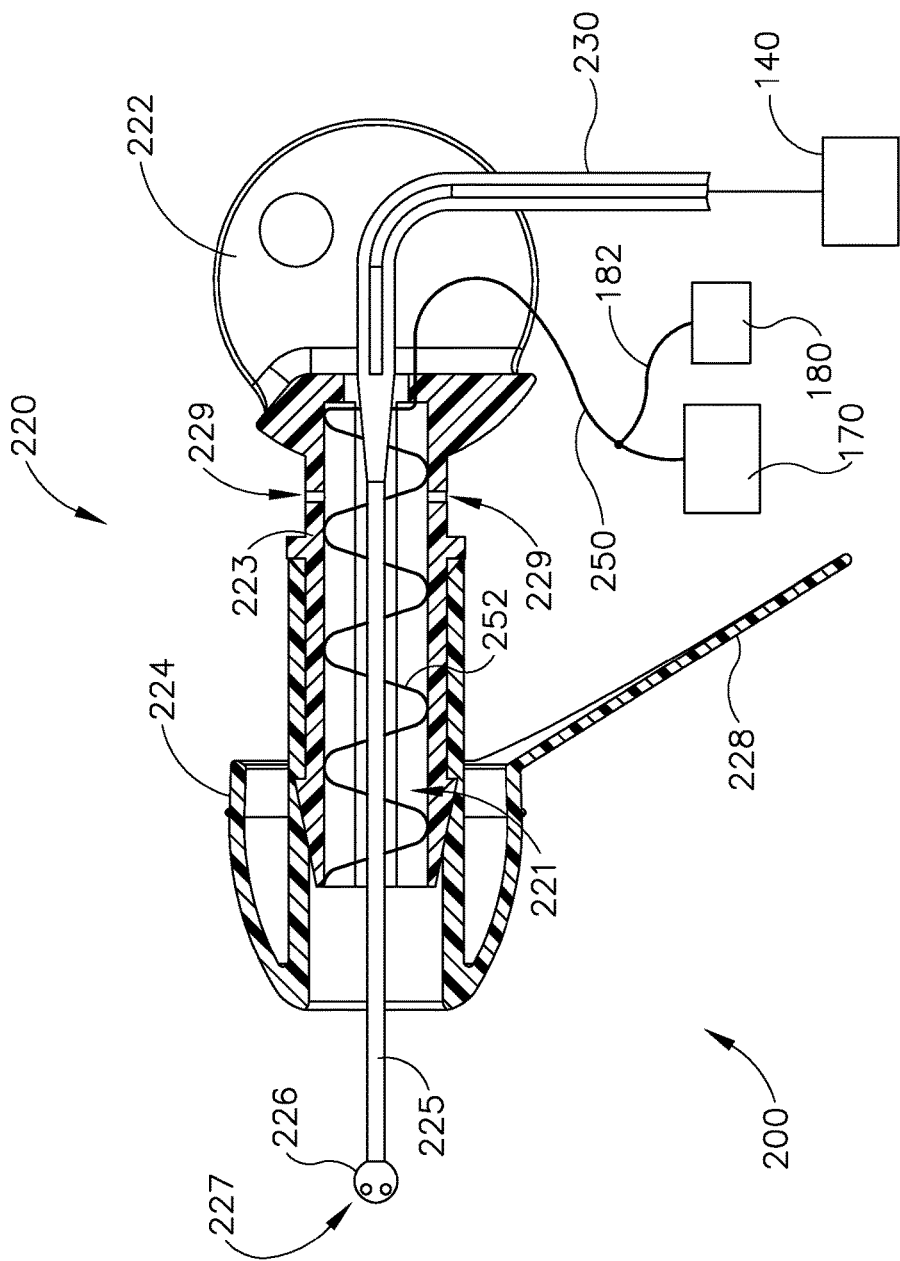
FIG. 6 depicts a side cross-sectional view of the earplug of FIG. 5.

In some versions, earplug (220) is configured and operable in accordance with at least some of the teachings of U.S. Pat. App. No. 13/827,403, entitled "Adhesive Earplugs Useful for Sealing the Ear Canal," filed on Mar. 14, 2013, the disclosure of which is incorporated by reference herein. As best seen in FIG. 6, earplug (220) of the present example includes a flexible sealing element (224) and a distally projecting nozzle (226). Sealing element (224) is configured to provide a fluid tight seal against the patient's ear canal when earplug (220) is inserted in the patient's ear canal. Nozzle (226) is positioned to project into the patient's ear canal when earplug (220) is inserted in the patient's ear canal, such that nozzle (226) is spaced lateral to the tympanic membrane (TM). Nozzle (226) has spray apertures (227) and is secured to the distal end of a semi-rigid post (225). Post (225) provides a path for fluid communication from conduit (230) to spray apertures (227). Spray apertures (227) are thus in fluid communication with fluid source (140) via post (225) and conduit (230). Sealing element (224) is secured to a rigid frame (223), which defines gripping features (222). Sealing element (224) and frame (223) also together define a working channel (221). Frame (223) defines a plurality of vent paths (229) in fluid communication with working channel (221). Vent paths (229) are configured to allow air to escape working channel (221) while working channel (221) fills with iontophoresis solution; yet are further configured prevent iontophoresis solution from escaping working channel (221) via vent paths (229) once working channel (221) is filled with iontophoresis solution. An iontophoresis electrode (252) in the form of a coil extends along at least part of the length of working channel (221). It should be understood that iontophoresis electrode (252) may have any other suitable configuration.

Iontophoresis electrode (252) is coupled with control unit (170) via a cable (250) and is thereby operable to be activated with a positive voltage as described above. Thus, control unit (170) may activate iontophoresis electrode (252) to provide an electrorepulsive force to the iontophoresis solution ions delivered through apertures (227), to drive the anesthetic of the iontophoresis solution ions into the tympanic membrane (TM) for anesthetization of the tympanic membrane (TM) as described above.

It should be understood that the above described iontophoresis systems (100, 200) may be varied in numerous ways. Several examples of how iontophoresis systems (100, 200) may be varied will be described in greater detail below, while still other examples will be apparent to those of ordinary skill in the art in view of the teachings herein. While the various iontophoresis systems described herein have been mentioned in relation to PETDD (10) and PE tube (20) delivery, it should be understood that any of the iontophoresis systems described herein may be used before a manual delivery of a PE tube (20), such that the iontophoresis systems described herein do not necessarily need to be used in conjunction with a PETDD (10). It should also be understood that iontophoresis systems may be used in various other clinical contexts, such that the iontophoresis systems described herein do not necessarily need to be used in the context of a PE tube (20) delivery or in other procedures in a patient's ear. The teachings herein may be readily applied to iontophoresis systems that are used in various other procedures and in various other parts of the human anatomy. Alternative systems and settings in which the teachings herein may be applied will be apparent to those of ordinary skill in the art.

III. Exemplary Fluid Flow Variations for Iontophoresis System

Figure 7:
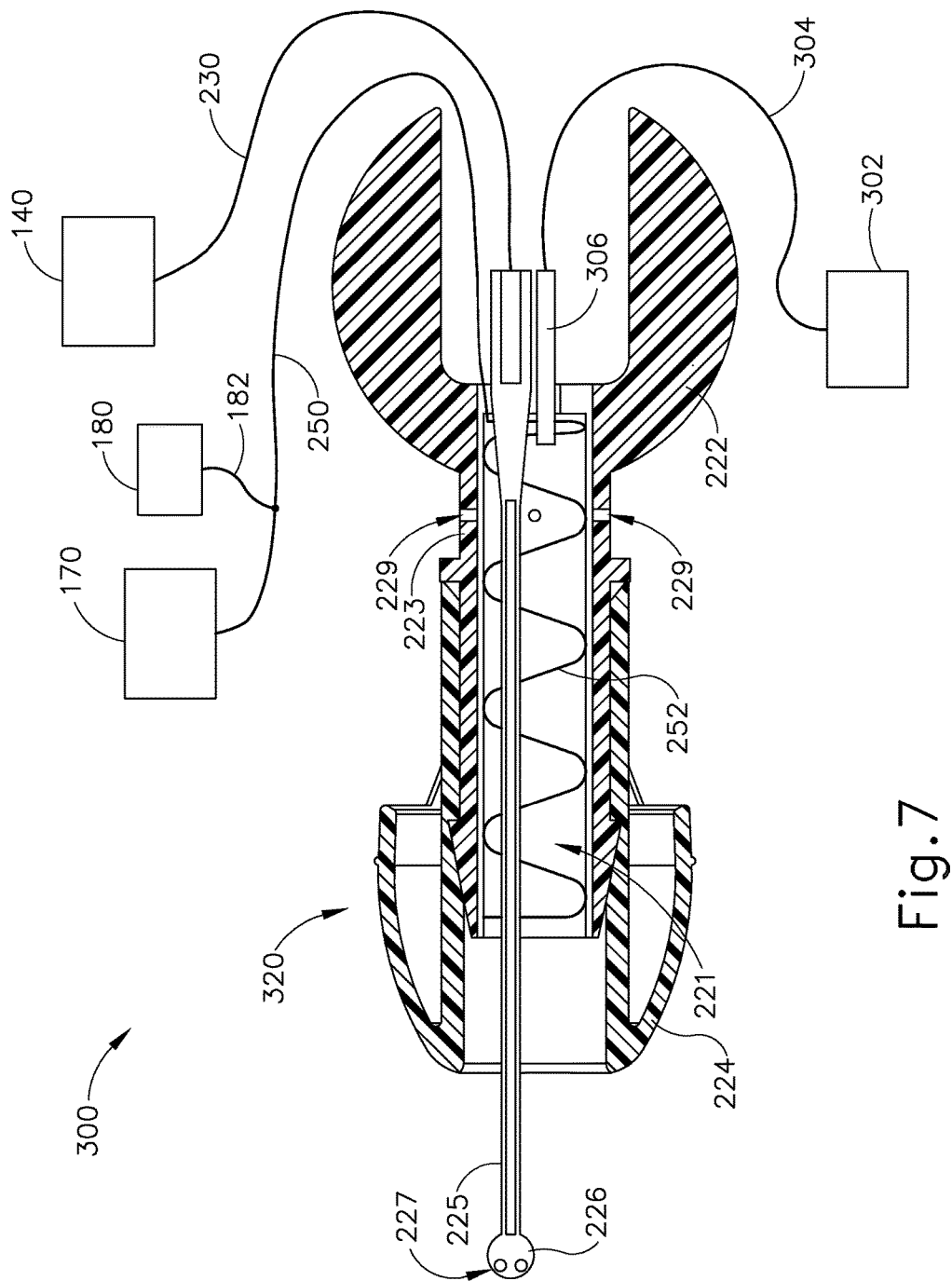
FIG. 7 depicts a schematic view of an exemplary iontophoresis system with continuous flow.

FIG. 7 depicts another exemplary iontophoresis system (300) that may be used to anesthetize a patient's tympanic membrane (TM), such as before a inserting a PE tube (20) into the tympanic membrane (TM) as described above. Iontophoresis system (300) of this example comprises an earplug (320), fluid source (140), control unit (170), and ground pad (180). Earplug (320) of this example is substantially similar to earplug (220) described above. In particular, earplug (320) of this example includes working channel (221), gripping features (222), rigid frame (223), sealing element (224), semi-rigid post (225), nozzle (226) with spray apertures (227), and electrode (252), respectively, as described above. Thus, the operability of these features will not be repeated here. Unlike earplug (220), however, earplug (320) of this example includes a drainage port (306) at the otherwise closed end of working channel (221) at the end of rigid frame (223).

Iontophoresis system (300) of this example further includes a drainage reservoir (302) that is coupled with a drainage conduit (304). Drainage conduit (304) is further coupled with drainage port (306). Drainage port (306) and drainage conduit (304) are configured to provide drainage of iontophoresis solution from working channel (221) into reservoir (302). This drainage enables additional, fresh iontophoresis solution to flow from fluid source (140) into the patient's ear during the activation of electrode (252). Thus, iontophoresis solution may flow substantially continuously through the patient's ear canal and through working channel (221) during the iontophoresis process. Keeping the iontophoresis solution fresh in the patient's ear canal and through working channel (221) in this manner may reduce or eliminate a drop in pH that might otherwise occur in some other systems. This may further enable practitioners to use non-buffered iontophoresis solution for iontophoresis solution, which may be more effective and/or efficient at providing anesthesia. Furthermore, the amount of time required for effective anesthesia via iontophoresis may decrease when unbuffered, fresh iontophoresis solution is used.

Figure 8:
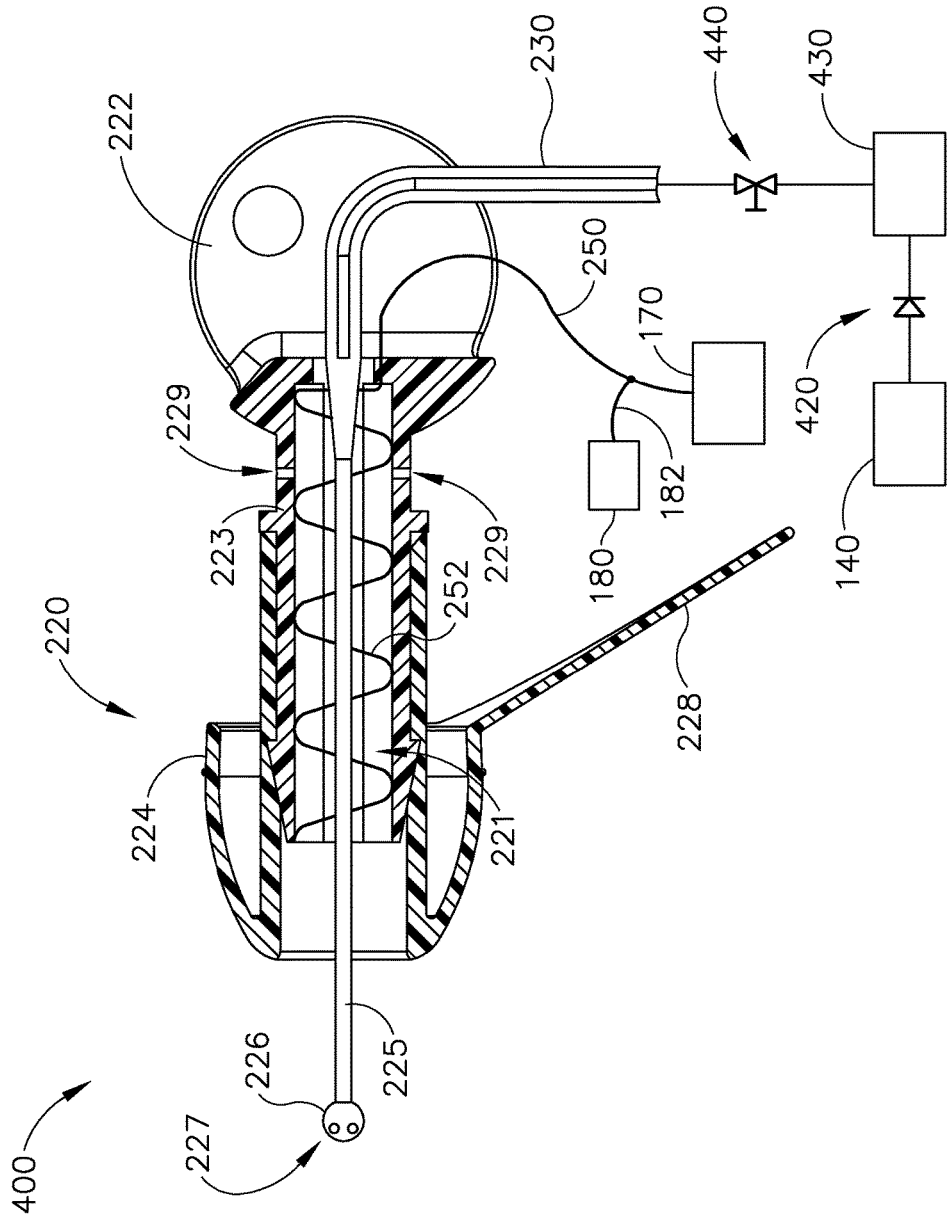
FIG. 8 depicts a schematic view of an exemplary iontophoresis system with a bolus actuator.

In some instances, it may be desirable to selectively provide a bolus of iontophoresis solution to the patient's ear canal during an iontophoresis process. By way of example only, this may be desirable to alleviate discomfort that the patient might experience during the ramp up of current delivery through electrode (252). FIG. 8 depicts an exemplary iontophoresis system (400) that may be used to provide such a bolus while anesthetizing a patient's tympanic membrane (TM), such as before a inserting a PE tube (20) into the tympanic membrane (TM) as described above. Iontophoresis system (400) of this example comprises an earplug (420), fluid source (140), control unit (170), and ground pad (180). Earplug (420) of this example is the same as earplug (220) described above, so the details and operability of its features will not be repeated here.

Iontophoresis system (400) of this example further comprises a check valve (420), a bolus delivery device (430), and a slide clamp (440). Check valve (420) is positioned in the fluid path between fluid source (140) and bolus delivery device (430). Slide clamp (440) is positioned on conduit (230), which provides a fluid path between bolus delivery device (430) and post (225). Bolus delivery device (430) is operable to deliver a bolus of a predetermined volume of iontophoresis solution to conduit (230); and thereby to the patient's ear canal. By way of example only, bolus delivery device (430) may comprise a reservoir configured to hold between approximately 3 cc and approximately 6 cc of iontophoresis solution. In some versions, bolus delivery device (430) comprises a bladder pump. Bolus delivery device (430) may be formed of a compliant material such that an operator may squeeze bolus delivery device (430) to drive a bolus of iontophoresis solution out from bolus delivery device (430) and through conduit (230) when slide clamp (440) is in an open position. In some instances, bolus delivery device (430) is formed of an elastic material or has some other resilient bias that drives iontophoresis solution from bolus delivery device (430) through conduit (230). In addition or in the alternative, bolus delivery device (430) may be squeezed or otherwise affirmatively actuated to drive iontophoresis solution from bolus delivery device (430) through conduit (230). Various suitable forms that bolus delivery device (430) may take will be apparent to those of ordinary skill in the art in view of the teachings herein. Bolus delivery device (430) may be initially filled or primed at the same time ear plug (220) is initially filled or primed.

Check valve (420) regulates the flow of iontophoresis solution from fluid source (140) into bolus delivery device (430). In particular, check valve (420) is configured to permit iontophoresis solution to flow only toward bolus delivery device (430) from fluid source (140). Check valve (420) is also configured to prevent the flow of fluid from fluid source (140) to bolus delivery device (430) until the fluid pressure of the iontophoresis solution reaches a cracking pressure associated with check valve (420). In particular, the cracking pressure of check valve (420) and the compliance of bolus delivery device (430) are selected such that check valve (420) stays open until approximately 3 cc of iontophoresis solution is dispensed from bolus delivery device (430), at which point check valve (420) closes. Any time the operator wishes to deliver a bolus of iontophoresis solution to the patient's ear canal, the operator may open slide clamp (440) and squeeze bolus delivery device (430).

This squeezing of bolus delivery device (430) overcomes the cracking pressure of check valve (420) and drives a bolus of iontophoresis solution to the patient's ear.

Slide clamp (440) is a conventional slide clamp and is operable to selectively open and close the fluid path provided by conduit (230). Slide clamp (440) thus prevents the free flow of iontophoresis solution from bolus delivery device (430) into conduit (230) until the operator is ready to provide additional iontophoresis solution to the patient's ear canal. Slide clamp (440) is open during initial filling of earplug (220) and the ear canal, but otherwise remains closed until the operator is ready to provide additional iontophoresis solution to the patient's ear canal. In some versions, an in-line air filter (not shown) is provided in the fluid path between bolus delivery device (430) and slide clamp (440), to prevent air bubbles from passing through conduit (230) into the patient's ear canal.

Some versions of iontophoresis system (400) may provide at least two modes of delivery, such as a continuous mode and a bolus mode. By way of example only, a continuous mode may be provided by a bolus delivery device (430) that is configured to self-actuate. For instance, this may be provided by a stretched bladder or resiliently loaded pump. The resilience of the material or some other driving feature may provide a relatively slow and gradual delivery of iontophoresis solution to conduit (230) (e.g., approximately 3 cc over a period of approximately 3 minutes, etc.) without intervention from the operator. In a bolus delivery mode, the same amount of iontophoresis solution (e.g., approximately 3 cc, etc.) may be delivered over a period of a few seconds through operator intervention (e.g., squeezing bolus delivery device (430), etc.). Other suitable ways in which iontophoresis system (400) may be configured and operable will be apparent to those of ordinary skill in the art in view of the teachings herein.

IV. Exemplary AC-Modulated Iontophoresis Signal.

As noted above, control unit (170) provides an electrical signal to the electrode (252) of earplug (120, 220, 320), to thereby create electrorepulsive forces for iontophoretic delivery of iontophoresis solution ions to/through the tympanic membrane (TM) and/or to/through other tissue within the patient's ear canal. In some forms of control unit (170), the electrical signal is in a DC form. In some instances, using DC current may require relatively high voltages to overcome resistance presented by tympanic membrane (TM). Such high voltages may be undesirable in some instances. The circuitry that may be required in order to provide suitable DC current to the electrode (252) of earplug (120, 220, 320) may also be relatively complex in some instances, such as by requiring high voltage op-amps, differential amplifiers, and/or other components that may be difficult to incorporate into low voltage highly integrated chips.

Figure 9:
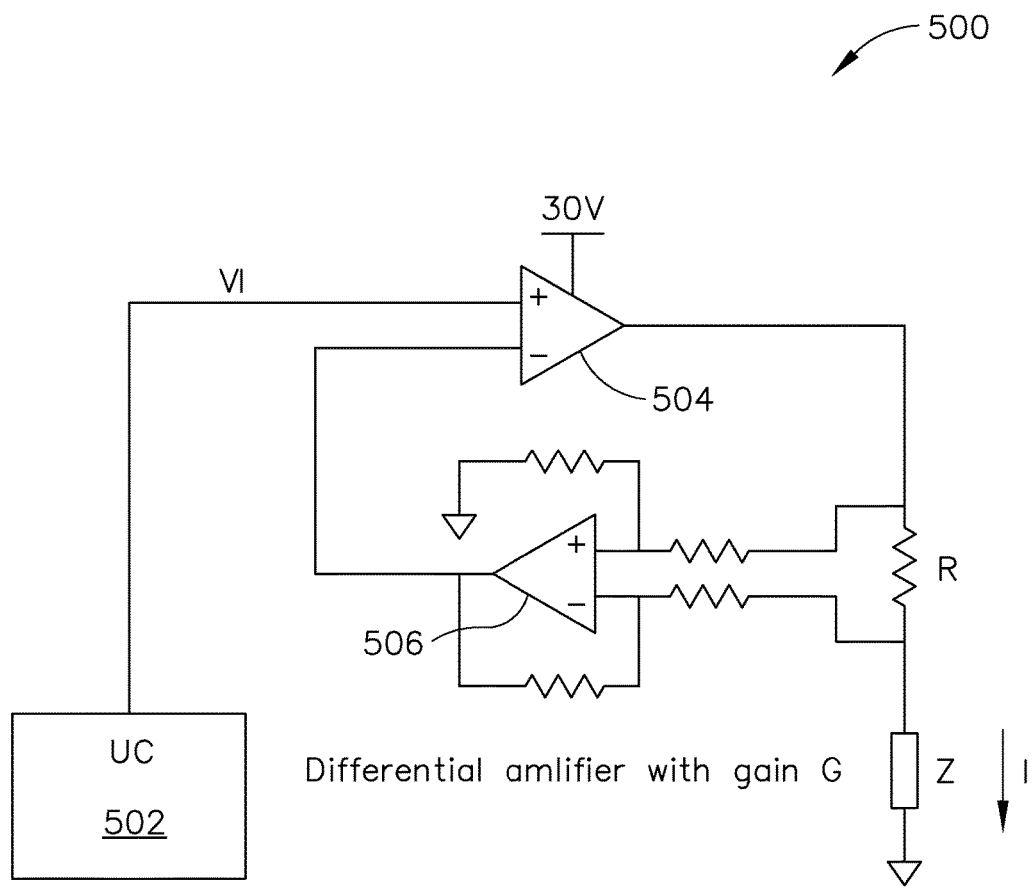
FIG. 9 depicts a circuit diagram of an exemplary iontophoresis signal generator for one channel in the system of FIG. 5.
Figure 10:
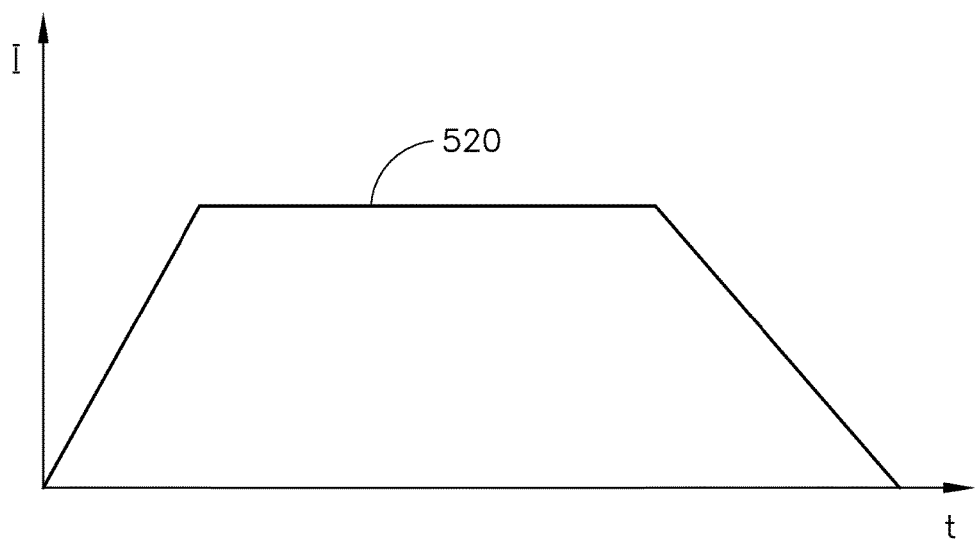
FIG. 10 depicts a signal diagram of current versus time associated with the generator of FIG. 9.

FIG. 9 depicts an iontophoresis driving circuit (500) associated with a control unit (170) of an exemplary DC based iontophoresis system. This exemplary circuit (500) may be used to impose a time-variant current I, an example of which is illustrated as curve (520) in FIG. 10, on the iontophoresis solution. A microcontroller (502) provides input voltage $V_i$ to an op-amp (504), which is configured with another op-amp (506), resistor R, and a network of other resistors to operate as a differential amplifier with gain G. The tympanic membrane (TM), or more generally the patient's body, is represented as impedance Z in FIG. 9 (and in FIGS. 11-13, 15, and 17). The current through resistor R is measured by the differential amplifier and is fed into op-amp (504) to regulate the current through the tympanic membrane (Z). In some instances, the input voltage $V_i$ is realized by a PWM signal generated by microcontroller (502). In some implementations, the DC current supplied by circuit (500) is ramped up until it reaches a current of approximately 1 mA. The current remains at 1 mA for a period of time, then is ramped down to zero, as illustrated in FIG. 10. 1 mA of DC is at the edge of electrical sensation for many persons, and some patients may feel discomfort during the iontophoresis process from the use of this amount of DC current. Similarly, some DC implementations may provide a relatively high current density at a ground return patch applied to the patient, which may result in skin burning effects.

In some other versions of control unit (170), the electrical signal is in an AC form or an AC modulated DC form. Merely illustrative examples of such systems will be described in greater detail below. It should be understood that some versions of such AC based iontophoresis systems may provide relatively more efficient iontophoresis through the tympanic membrane (TM), such that a relatively lower voltage and/or relatively lower current may be used. In addition or in the alternative, some versions of such AC based iontophoresis systems may improve the transfer of ions of interest versus background electrolyte ions. Transfer effectiveness may be based on pore size, pore size distribution, and pore surface charge density, which may in turn be influenced by AC stimulus. Some versions of AC based iontophoresis systems may also have less sensation impact on the patient and/or may be less sensitive to inter-patient and intra-patient variability.

Figure 11:
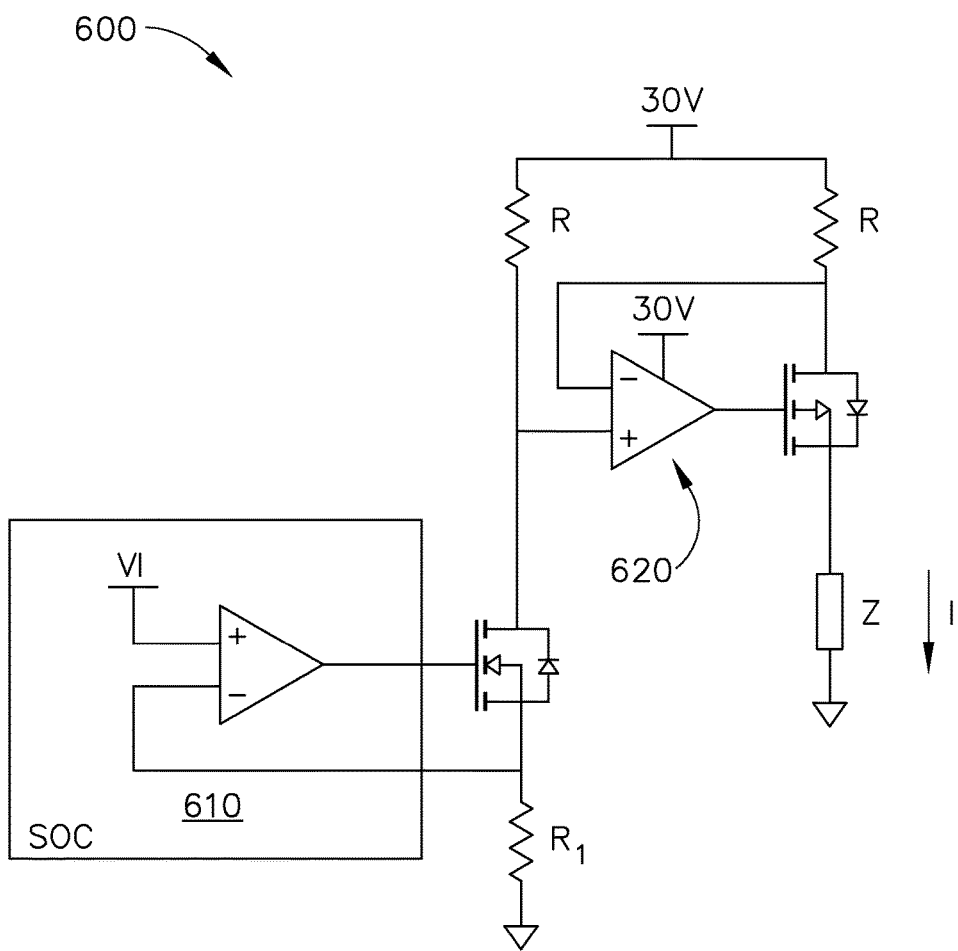
FIG. 11 depicts a circuit diagram of another exemplary iontophoresis signal generator for use in the system of FIG. 5.

FIG. 11 shows another exemplary iontophoresis driving circuit (600) that may be incorporated into control unit (170). In circuit (600) of this example, input $V_i$ to system-on-a-chip (SOC) (610) and resistance $R_1$ control the output current I without needing a high-voltage differential amplifier. Still, circuit (600) uses a high-voltage op-amp (620) in this example.

Figure 12:
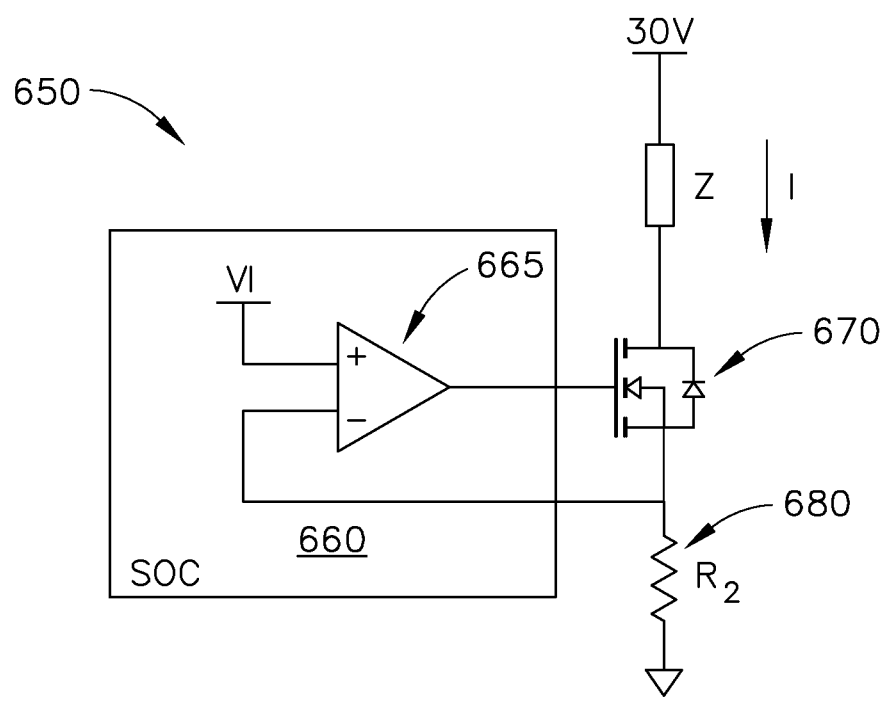
FIG. 12 depicts a circuit diagram of yet another exemplary iontophoresis signal generator for use in the system of FIG. 5.

FIG. 12 shows yet another exemplary iontophoresis driving circuit (650) that may be incorporated into control unit (170). Circuit (650) of this example provides a current sink such that the current is pulled through the load (Z) (e.g., the tympanic membrane (TM)), using input voltage $V_i$ as a noninverting input to a low voltage op-amp (665) in a SOC (660). A transistor (670) is coupled with the output of op-amp (665). Transistor (670) is further coupled with the load (Z) and a resistor (680), and further provides the inverting input to op-amp (665). In this example, transistor (670) handles the higher voltage at a significantly lower cost, both in terms of component cost and space on a printed circuit board (PCB) implementation of circuit (650). It should be understood that, by using a current sink approach, circuit (650) operates at a lower voltage than what might otherwise be required using a current source approach.

Figure 13:
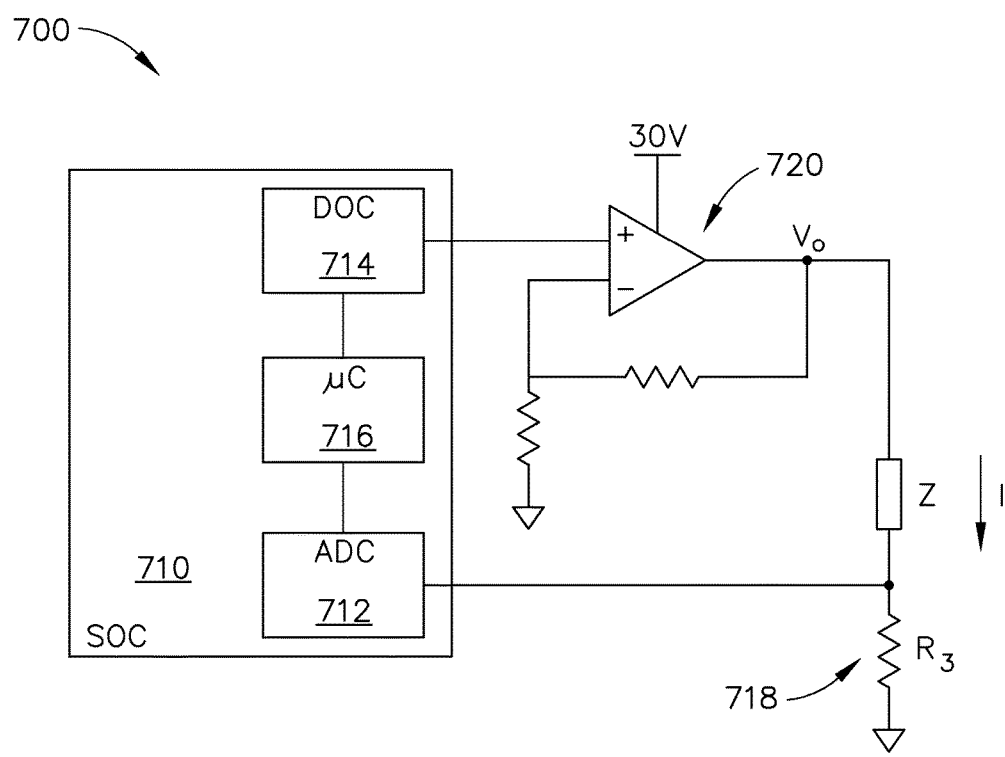
FIG. 13 depicts a circuit diagram of yet another exemplary iontophoresis signal generator for use in the system of FIG. 5.

FIG. 13 shows an exemplary iontophoresis driving circuit (700) that also provides a current sink through a microcontroller feedback loop with microcontroller control of an op-amp (720). In this exemplary circuit (700), there is no need for a DC source in the analog electronics. Instead, the current I is sensed by a series resistor (718) and fed to an analog-digital converter (ADC) (712) on a SOC (710), and the ADC (712) sends its digital output to a microcontroller (716) on SOC (710). Microcontroller (716) responsively controls a digital-analog converter (DAC) (714) to provide a noninverting input to op-amp (720), to thereby produce an output voltage $V_o$ at the output of op-amp (720). In the present example, sense resistor (718) is put on the ground side of load (Z) (e.g., the tympanic membrane (TM)). In an exemplary alternative configuration of circuit (700), sense resistor (718) is put on the higher-voltage side of the patient's body (Z) to be fed into ADC (712) inside SOC (710) using a resistor divider (not shown).

Figure 14:
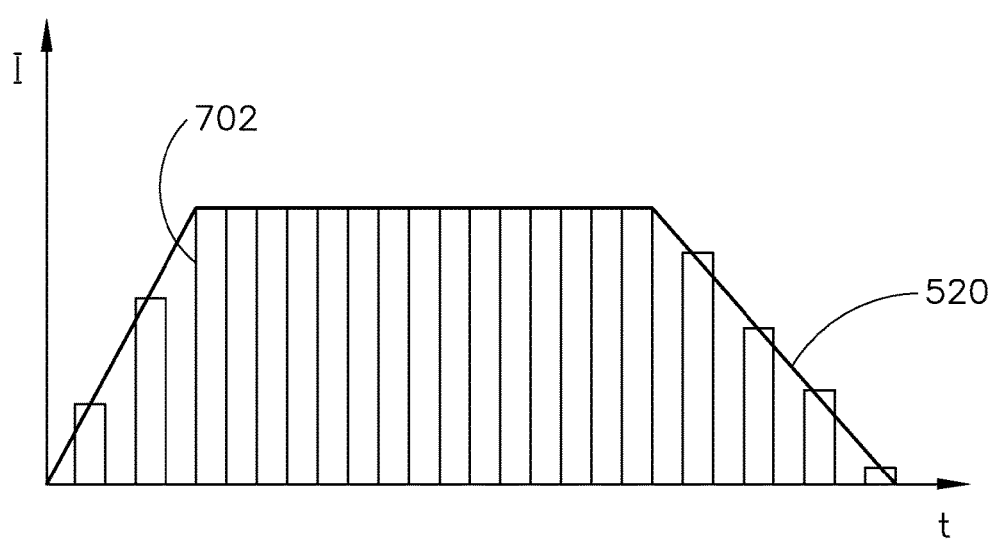
FIG. 14 depicts a signal diagram of current versus time associated with another exemplary iontophoresis signal generator for use in the system of FIG. 5.

FIG. 14 shows an exemplary signal (702) that may be provided through circuit (700). A DC signal (520) (see FIG. 10) is modulated by circuit (700) with an AC signal to yield a modulated current signal (702). Modulated current signal (702) applies a pulsed AC signal in the form of a square wave in the present example. However, it should be understood that modulated current signal (702) may have a variety of other forms, including but not limited to a sinusoidal waveform, a sawtooth waveform, a trapezoidal waveform, etc. By way of example only, modulated current signal (702) may be processed using circuit (650) (from FIG. 12), using circuit (700) (from FIG. 13), and/or using any other suitable circuit.

Some versions of control unit (170) may use two separate channels to anesthetize the patient's two ears at the same time. In some such versions, both channels are not operational at the same time because they both use the same ground pad (180) as a return electrode on the patient's skin. Even if two ground pads (180) were used, the body may effectively connect the two ground pads (180) together. Control unit (170) may thus alternate between the two channels by providing pulsed current such that only one channel is active at a particular instant. The frequency of alternation between the two channels may nevertheless be fast enough to effectively function as simultaneous activation. In other words, the two channels may seem to be activated simultaneously even though they are in fact discretely activated in a rapidly alternating fashion. It should be understood that each channel in a two channel system may have its own instance of the driving circuit (500, 600 650, 700). Alternatively, a single instance of the driving circuit (500, 600 650, 700) may be used to drive both channels.

Figure 15:
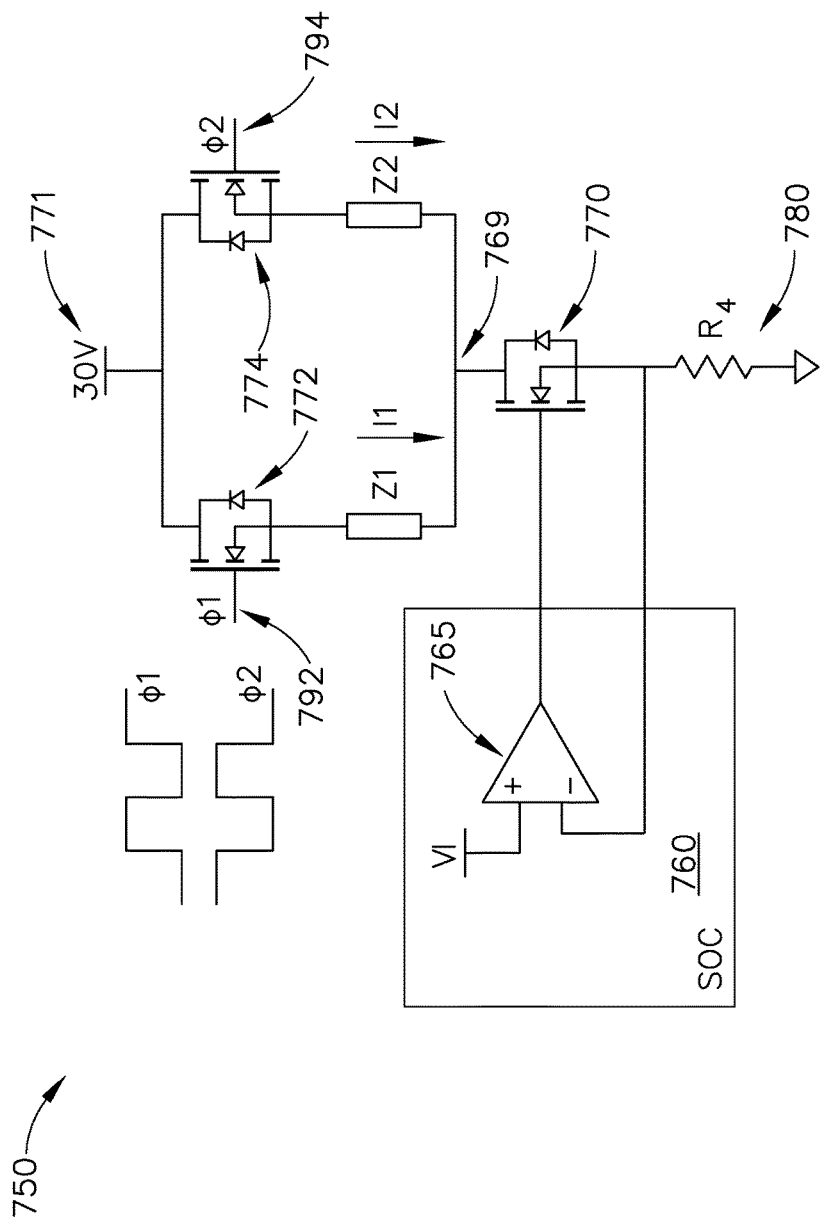
FIG. 15 depicts a circuit diagram of an exemplary two-channel iontophoresis signal generator for use in the system of FIG. 5.

FIG. 15 shows an exemplary iontophoresis driving circuit (750) that enables two separate channels (for the patient's two ears) to be effectively activated substantially simultaneously (in a rapidly alternating fashion) as noted above. Circuit (750) of this example includes a current sink architecture like the one provided through circuit (650) of FIG. 12; yet circuit (750) alternates the current sink between a first channel for an electrode in one of the patient's ears (Z1) and a second channel for an electrode in the other one of the patient's ears (Z2) such that current is only being drawn through one of the two channels at any given instant. Circuit (750) of this example includes a system-on-a-chip (SOC) (760) with a low-voltage op-amp (765). A transistor (770) is coupled with the output of op-amp (765). Transistor (770) is further coupled with an output node (769) and a resistor (780), and further provides the inverting input to op-amp (765). SOC (760) produces current through resistor (780) as discussed above, but the current is pulsed and split between the two channels via output node (769) as current I1 and I2.

Output node (769) receives the switched current for the electrode associated with each ear (Z1, Z2). In particular, a first transistor (772) is coupled with a voltage source (771) and the electrode for one ear (Z1). First transistor (772) is clocked (i.e., alternatingly switched on and off) through a first input (792) with a first clocking gate signal ($\phi 1$). A second transistor (774) is coupled with voltage source (771) and the electrode for the other ear (Z2). Second transistor (774) is clocked (i.e., alternatingly switched on and off) through a second input (794) with a second clocking gate signal ($\phi 2$). In this example, gate signals ($\phi 1$, $\phi 2$) are 180 degrees out of phase with each other, such that they are non-overlapping. Each current can be set independently by voltage $V_i$ generated by SOC (750) and the resistor R4 (780).

Figure 16:
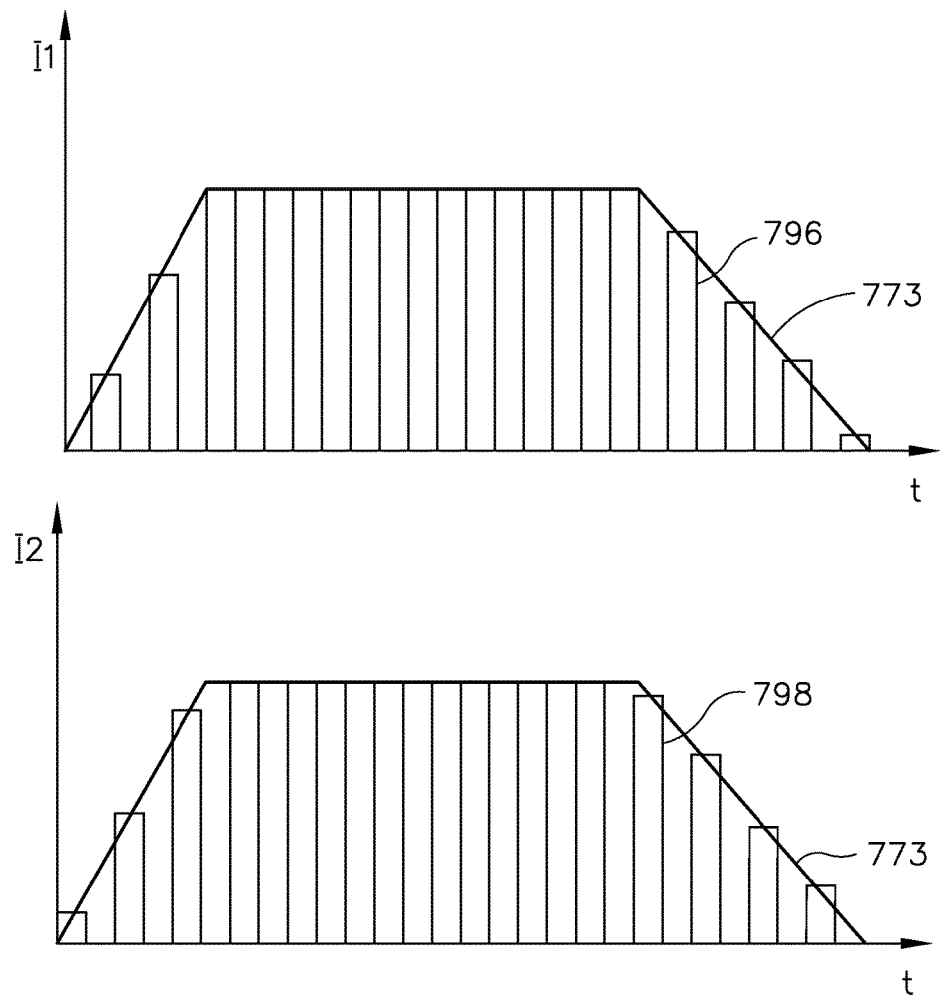
FIG. 16 depicts a signal diagram of current versus time associated with the generator of FIG. 15.

FIG. 16 shows signals (796, 798) that may be provided through circuit (750) to generate the separate currents (I1, I2) for the respective electrodes associated with the patient's ears (Z1, Z2). DC signal (773) is modulated by circuit (750) to provide the separate modulated current signals (796, 798). It should be understood from the foregoing that, at any given instant, only one ear (Z1, Z2) receives a current pulse while the other does not. While the electrodes in ears (Z1, Z2) are not both actually active at the exact same instant, the frequency of the pulses may provide a practical effect of substantially simultaneous activation of both electrodes.

In some instances, driving circuit (750) may produce a built-up charge in the patient's body during an iontophoresis process. In particular, the patient's body may act like capacitor through skin polarization. A charge buildup in the patient could result in an electric sensation in the patient (e.g., in the patient's ear and at the location of ground patch (180)) when the current (I1, I2) is turned off. Accordingly, it may be desirable to provide a current path that provides a discharge route as soon as the current (I1, I2) is turned off, such that charge does not build up in the patient. This may reduce the amount of patient sensation during an iontophoresis process.

Figure 17:
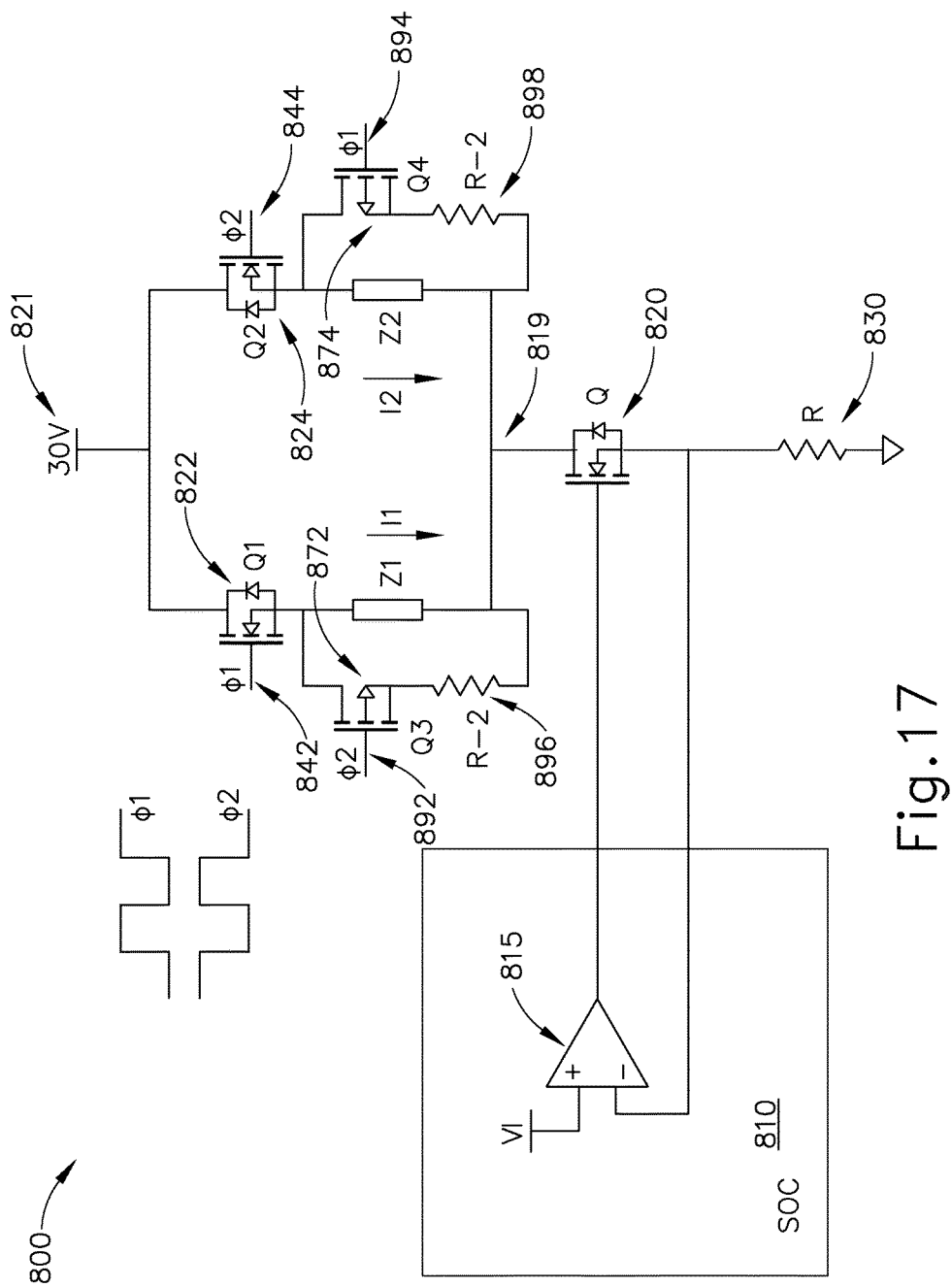
FIG. 17 depicts a circuit diagram of another exemplary two-channel iontophoresis signal generator for use in the system of FIG. 5.

FIG. 17 shows yet another exemplary iontophoresis driving circuit (800) that includes discharge features for the channels associated with each ear (Z1, Z2). Circuit (800) enables two separate channels (for the patient's two ears (Z1, Z2)) to be effectively activated substantially simultaneously (in a rapidly alternating fashion) as noted above. Circuit (800) of this example is substantially similar to circuit (750) described above. Circuit (800) of this example includes a current sink architecture like the one provided through circuit (750), including alternating the current sink between a first channel for an electrode in one of the patient's ears (Z1) and a second channel for an electrode in the other one of the patient's ears (Z2) such that current is only being drawn through one of the two channels at any given instant. Circuit (800) of this example includes a system-on-a-chip (SOC) (810) with a low-voltage op-amp (815). A transistor (820) is coupled with the output of op-amp (815). Transistor (820) is further coupled with a load output (819) and a resistor (830), and further provides the inverting input to op-amp (815). SOC (810) produces current through resistor (830) as discussed above, but the current is pulsed and split between the two channels via load output (769) as current I1 and I2.

Load output (819) receives the switched load for the electrode associated with each ear (Z1, Z2). In particular, a first transistor (822) is coupled with a voltage source (821) and the electrode for one ear (Z1). First transistor (822) is clocked (i.e., alternatingly switched on and off) through a first input (842) with a first clocking gate signal ($\phi 1$). A second transistor (824) is coupled with voltage source (821) and the electrode for the other ear (Z2). Second transistor (824) is clocked (i.e., alternatingly switched on and off) through a second input (844) with a second clocking gate signal ($\phi 2$). In this example, gate signals ($\phi 1$, $\phi 2$) are 180 degrees out of phase with each other, such that they are non-overlapping. It should be understood that circuit (800) may produce signals in each channel that are the same as signals (796, 798) described above and shown in FIG. 16. In other words, at any given instant, only one ear (Z1, Z2) receives a current pulse while the other does not. While the electrodes in ears (Z1, Z2) are not both actually active at the exact same instant, the frequency of the pulses may provide a practical effect of substantially simultaneous activation of both electrodes.

Unlike circuit (750), circuit (800) of the present example also includes additional transistors (872, 874) and resistors (896, 898). Transistor (872) is coupled with the electrode for first ear (Z1), downstream of transistor (822). Transistor (872) is configured to provide a discharge path for first ear (Z1) when the pulsed current for first ear (Z1) is off. In particular, transistor (872) has an input (892) that is clocked with second clocking gate signal (φ2). Transistor (872) and resistor (896) are configured to discharge any charge built up through the electrode of first ear (Z1) when transistor (872) is switched on by second gate signal (φ2). Since gate signals (φ1, φ2) are 180 degrees out of phase with each other as noted above, it should be understood that the electrode of first ear (Z1) alternates between receiving a pulse of current (I1) and being discharged. In other words, the discharge path provided through transistor (872) and resistor (896) is opened each time current (I1) is zero. Resistor (896) in this example is simply added to control the resistance of the discharge path, though it should be understood that resistor (896) is merely optional.

Similarly, transistor (874) is coupled with the electrode for second ear (Z2), downstream of transistor (824). Transistor (874) is configured to provide a discharge path for second ear (Z2) when the pulsed current for second ear (Z2) is off. In particular, transistor (874) has an input (894) that is clocked with first clocking gate signal (φ1). Transistor (874) and resistor (898) are configured to discharge any charge built up through the electrode of second ear (Z2) when transistor (874) is switched on by first gate signal (φ1). Since gate signals (φ1, φ2) are 180 degrees out of phase with each other as noted above, it should be understood that the electrode of second ear (Z2) alternates between receiving a pulse of current (I2) and being discharged. In other words, the discharge path provided through transistor (874) and resistor (898) is opened each time current (I2) is zero. Resistor (898) in this example is simply added to control the resistance of the discharge path, though it should be understood that resistor (898) is merely optional.

Other suitable ways of providing AC driven iontophoresis will be apparent to those of ordinary skill in the art in view of the teachings herein.

V. Exemplary Air Bubble Detection in an Iontophoresis System

As noted above, earplug (120, 220, 320) includes an anode electrode (252) that is used to provide an electrorepulsive force for iontophoretic delivery of iontophoresis solution ions to/through a tympanic membrane (TM) and/or to/through other tissue within the patient's ear canal. In some instances, air bubbles may be trapped within earplug (120, 220, 320) as iontophoresis solution is communicated through earplug (120, 220, 320). Such air bubbles may present high impedance in the iontophoresis path, which may cause the system to degrade in performance. If an air bubble is trapped on the electrode, this may effectively reduce the surface area of the electrode, which may cause the current density at the rest of the electrode surface area to increase. Such an increase in current density may create out gassing, which may further generate a larger bubble and eventually cause degradation in performance. If an air bubble gets trapped against the tympanic membrane (TM) or elsewhere in the ear canal, it will reduce the effective surface area of the anesthetic delivery, thereby reducing the anesthetic effect of the iontophoresis process. It may therefore be desirable to take structural and/or procedural measures to prevent or otherwise reduce the occurrence of air bubbles getting trapped in earplug (120, 220, 320), such as by ensuring full immersion of the anode electrode (252) in iontophoresis solution; as well as full contact between the iontophoresis solution and the tympanic membrane (TM). This may include providing features operable to detect whether the anode electrode is fully immersed in iontophoresis solution, when an air bubble trapped on the anode electrode impedes electrical performance, and/or when an air bubble is on the tympanic membrane (TM).

Figure 18:
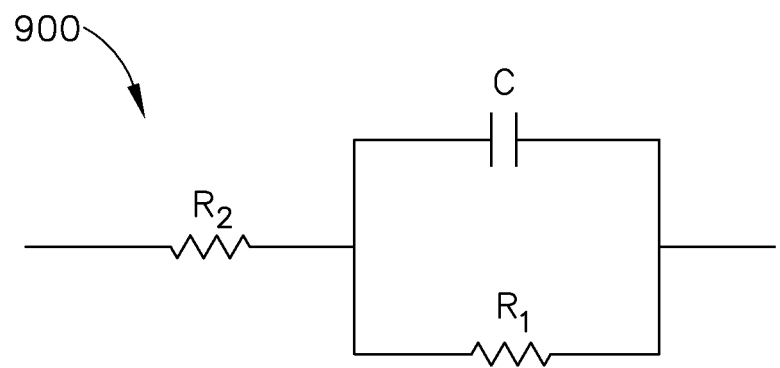
FIG. 18 depicts an equivalent circuit diagram for electrodes in an ionic solution.

FIG. 18 shows a simple equivalent electrical circuit (900) for electrodes in an ionic solution such as an iontophoresis solution. Circuit (900) includes double-layer capacitance C, resistance through the path at the junction of the electrode/electrolyte interface as R1, and the series resistance R2 due to the bulk resistance of the iontophoresis solution. It should be understood that R1 may be the equivalent of resistance through the path at the junction of anode electrode (252) and the iontophoresis solution. If there is an air bubble on an anode electrode (252) in the iontophoresis solution, the effective surface area of the electrode is reduced, and thus the double-layer capacitance C value is reduced. Thus, air bubbles may be detected through capacitance measurements.

Figure 19:
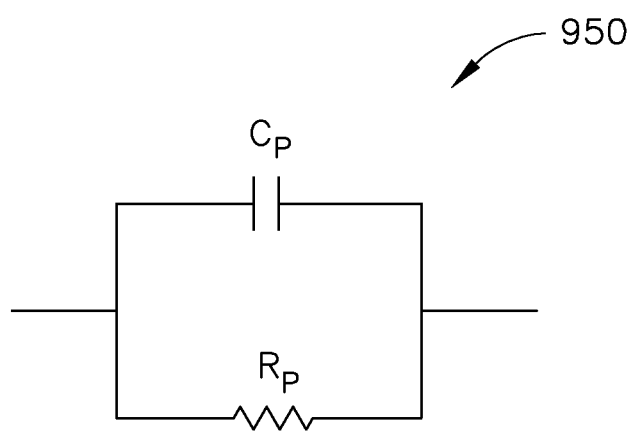
FIG. 19 depicts a circuit diagram approximating the circuit of FIG. 16 in certain circumstances.

In some versions, capacitance measurements may be based on parallel component impedance measurement. This technique may convert circuit (900) into the equivalent of a parallel RC circuit (950), as shown in FIG. 19. With reference to FIG. 19, since $C_p$ is measured, R2 may be selected to be low enough that $C_p$ is as close to C as possible. This may prevent masking of changes in C by high R2 series resistance. In order to obtain a low resistance R2, an auxiliary electrode may be placed in the same iontophoresis solution in the same ear canal as anode electrode (252). The placement of an auxiliary electrode may provide detection of air bubbles trapped in earplug (120, 220, 320) and/or elsewhere in the system. In order to provide a high capacitance signal value, a low-frequency (e.g., 100 Hz) sinusoidal waveform with magnitude 1 $V_{rms}$ may be used. With these parameters, a capacitance on the order of hundreds of nF to a few μF may be achievable. Further optimization of these parameters may yield an even better signal-to-noise ratio, as will occur to those skilled in the art. Various examples of how an auxiliary electrode may be incorporated into an earplug (120, 220, 320) for detection of air bubbles through capacitance measurements will be described in greater detail below, while other examples will be apparent to those of ordinary skill in the art in view of the teachings herein.

Figure 20:
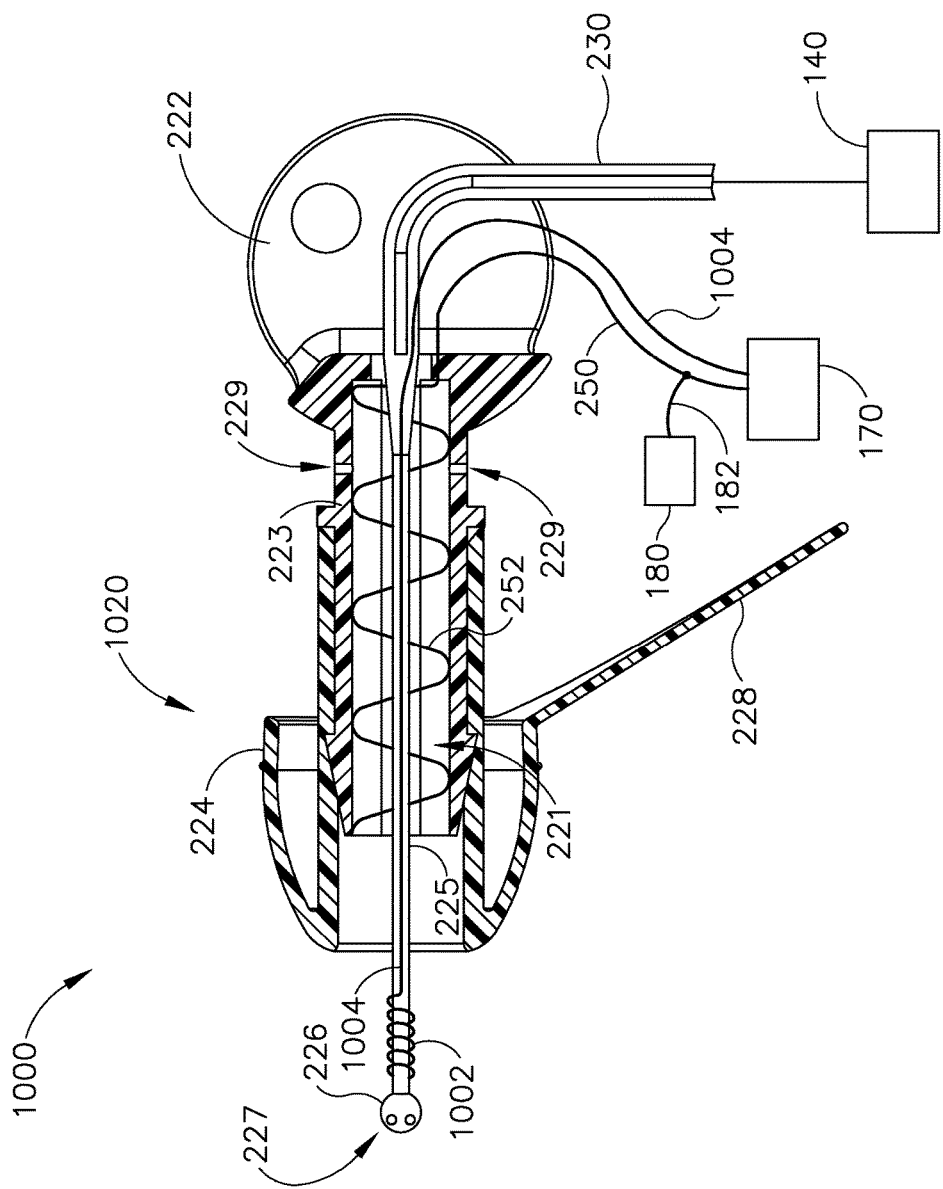
FIG. 20 depicts a side cross-sectional view of an exemplary iontophoresis plug with an auxiliary coil for detecting air bubbles around the coil electrode.

FIG. 20 shows an exemplary iontophoresis system (1000) that comprises an earplug (1020), a fluid source (140), control unit (170), and ground pad (180). Earplug (1020) of this example is substantially similar to earplug (220) described above. In particular, earplug (1020) of this example includes working channel (221), gripping features (222), rigid frame (223), sealing element (224), semi-rigid post (225), nozzle (226) with spray apertures (227), and electrode (252), as described above. Thus, the operability of these features will not be repeated here. Unlike earplug (220), however, earplug (1020) of this example includes an auxiliary electrode (1002) wrapped about a distal portion of post (225), just proximal to nozzle (226). Auxiliary electrode (1002) may be formed of silver, gold, and/or any other suitable conductor. Auxiliary electrode (1002) is in communication with control unit (170) via a wire (1004), which extends along post (225) in the present example. It should be understood that wire (1004) may extend within post (225) and/or along at least a portion of the exterior of post (225).

While wire (1004) is shown as extending through the proximal end of frame (223), it should be understood that wire (1004) may instead be routed through a vent path (229) or be otherwise routed.

As working channel (221) and the patient's ear canal fill with iontophoresis solution, anode electrode (252) and auxiliary electrode (1002) both become immersed in the iontophoresis solution and thereby form a capacitor, with the iontophoresis solution serving as an electrolyte. The capacitance of this capacitor is sensed and monitored by control unit (170). Since capacitance is directly proportional to the surface area of the electrodes (252, 1002) forming the capacitor, an air bubble may be detected as a reduction in capacitance since the air bubble will reduce the effective surface area of electrode (252). Certain fluctuations in capacitance may be expected even in the absence of air bubbles, so control unit (170) may be configured to sense when the capacitance value falls below a particular threshold value. That threshold value may of course be established based on a capacitance value that would be expected to indicate the presence of an air bubble. A suitable capacitance threshold value, or at least a method of determining a suitable capacitance threshold value for a particular system, will be apparent to those of ordinary skill in the art in view of the teachings herein.

Figure 21:
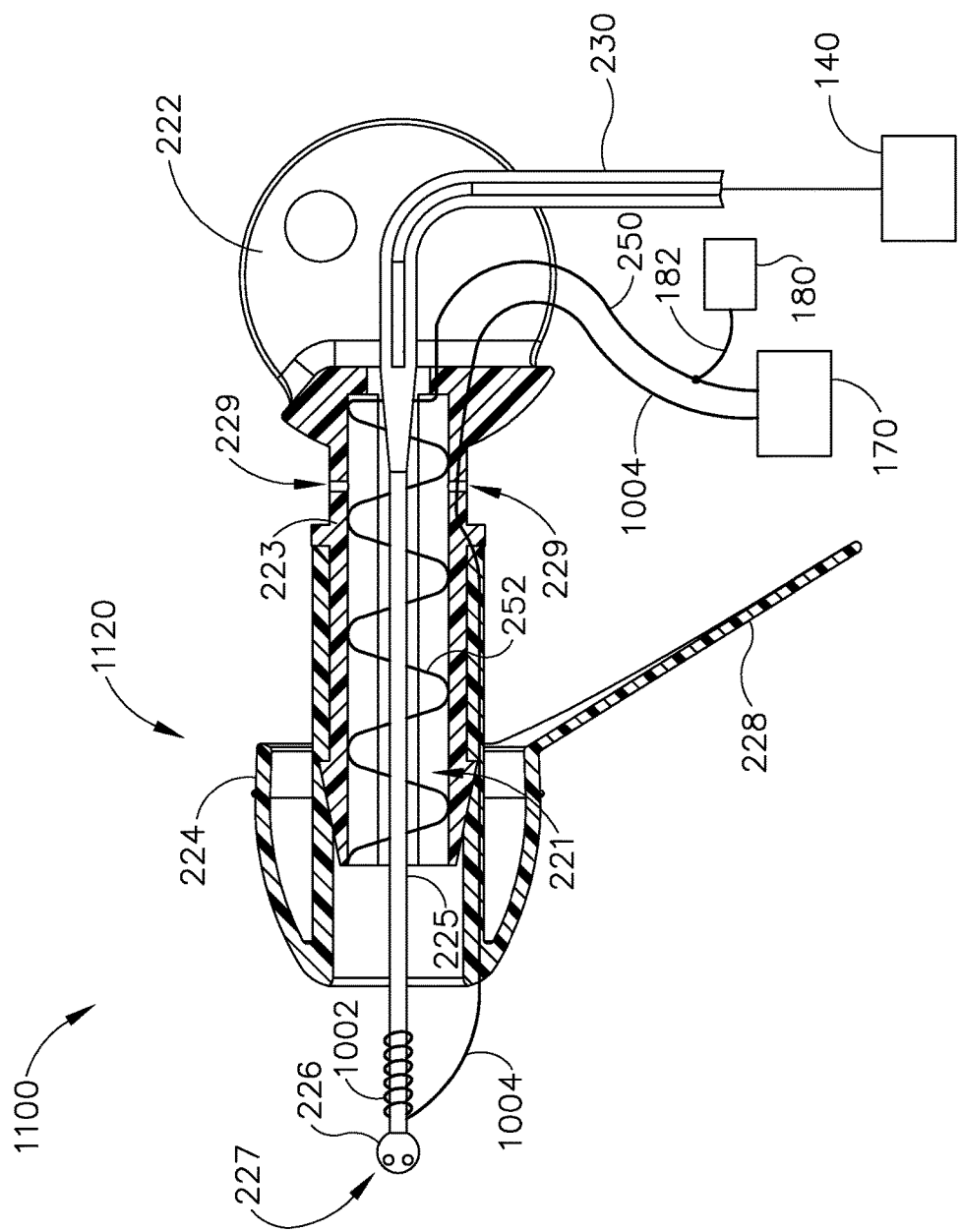
FIG. 21 depicts a side cross-sectional view of another exemplary iontophoresis plug with an auxiliary coil for detecting air bubbles around the coil electrode.

FIG. 21 shows an exemplary alternative iontophoresis system (1100) that comprises an earplug (1120), a fluid source (140), control unit (170), and ground pad (180). Earplug (1120) of this example is substantially similar to earplug (1020) described above. In particular, earplug (1120) of this example includes working channel (221), gripping features (222), rigid frame (223), sealing element (224), semi-rigid post (225), nozzle (226) with spray apertures (227), anode electrode (252), auxiliary electrode (1002), and wire (1004), as described above. Thus, the operability of these features will not be repeated here. Unlike earplug (1020), however, the wire (1004) in earplug (1120) of this example extends along sealing element (224) and rigid frame (223) instead of extending along post (225). While wire (1004) is shown as again extending through the proximal end of frame (223) in this example, it should be understood that wire (1004) may instead be routed through a vent path (229) or be otherwise routed.

Figure 22:
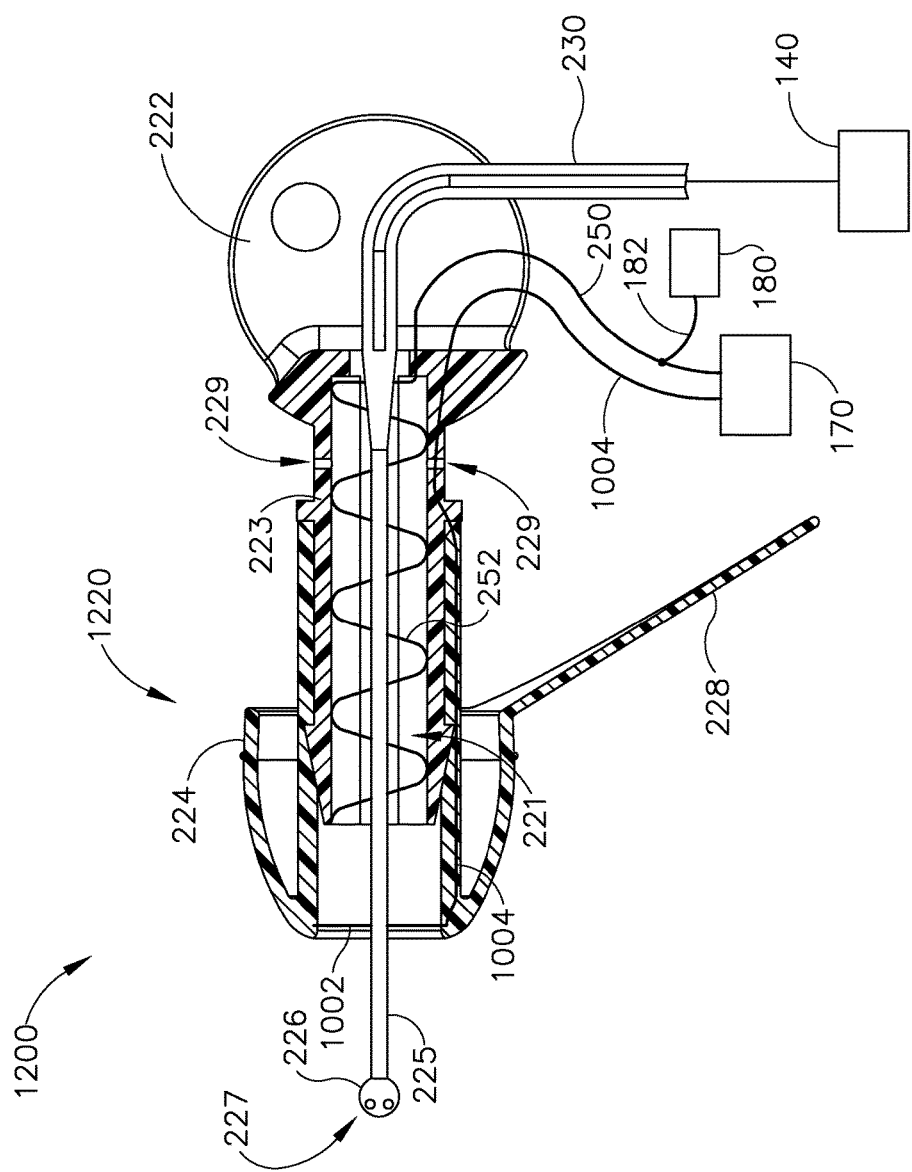
FIG. 22 depicts a side cross-sectional view of yet another exemplary iontophoresis plug with an auxiliary coil for detecting air bubbles around the coil electrode.

FIG. 22 shows yet another exemplary alternative iontophoresis system (1200) that comprises an earplug (1220), a fluid source (140), control unit (170), and ground pad (180). Earplug (1220) of this example is substantially similar to earplug (1120) described above. In particular, earplug (1220) of this example includes working channel (221), gripping features (222), rigid frame (223), sealing element (224), semi-rigid post (225), nozzle (226) with spray apertures (227), anode electrode (252), auxiliary electrode (1002), and wire (1004), as described above. Thus, the operability of these features will not be repeated here. Unlike earplug (1120), however, the auxiliary electrode (1002) in earplug (1220) of this example is secured to sealing element (224), at the inner diameter of sealing element (224) at the distal opening of working channel (221). This location may make auxiliary electrode (1002) more sensitive to bubbles in working channel (221) than it might be if positioned on the distal end of post (225) as shown in FIGS. 20-21.

Figure 23:
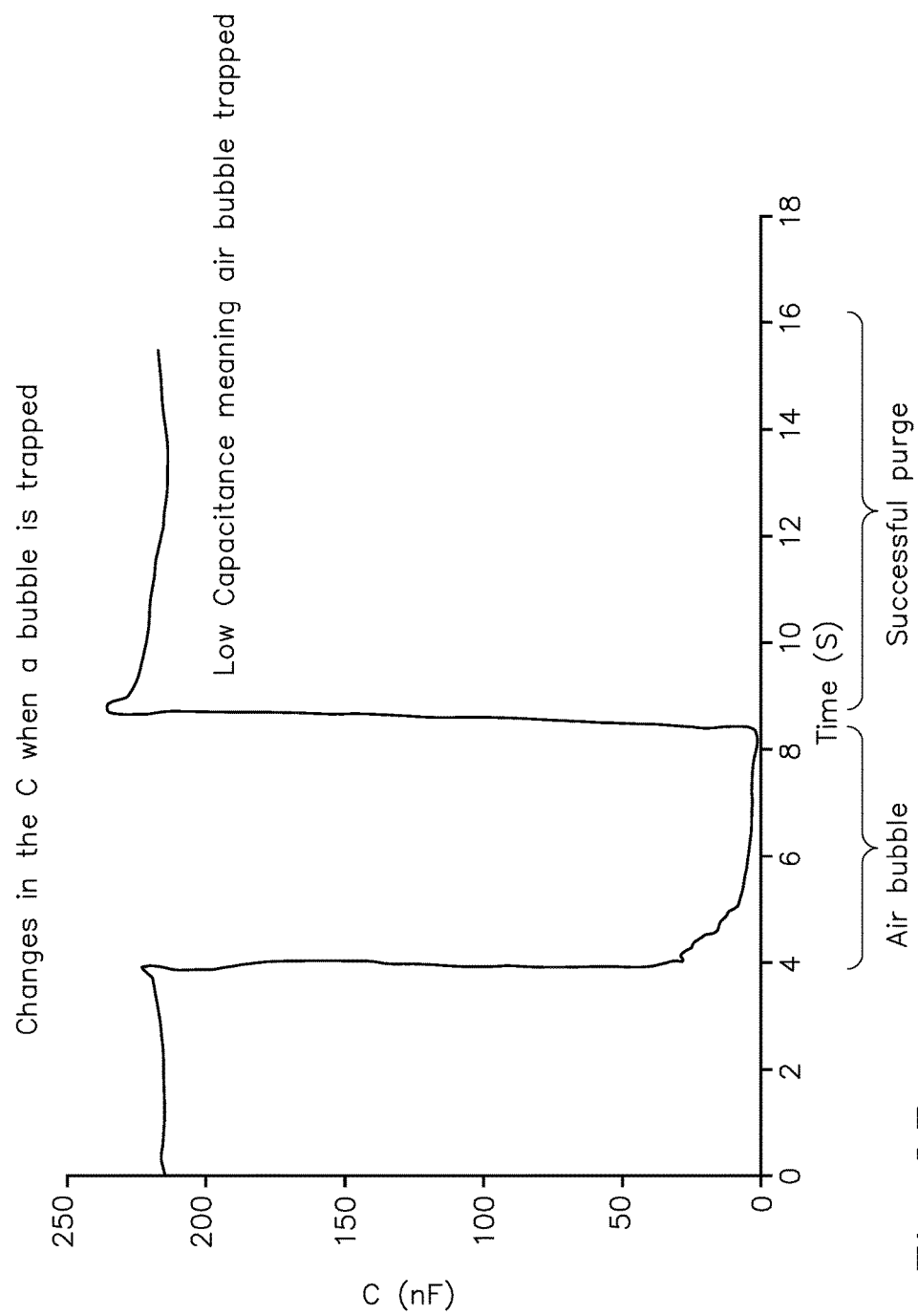
FIG. 23 depicts a signal diagram showing capacitance in the system of FIG. 20 over a period of time.

In any of the iontophoresis systems (1000, 1100, 1200) described above, control unit (170) may be configured to automatically provide a particular response when the capacitance level falls below a threshold value. By way of example only, control unit (170) may be operable to drive an operator feedback feature to alert the operator of an air bubble in earplug (1020, 1120, 1220). Such feedback may be audible (e.g., a tone, buzzer, etc.), visual (e.g., a light illuminating, a display providing a textual/graphic indication, etc.), and/or haptic (e.g., a handheld version of control unit (170) vibrating, etc.). Such feedback may prompt the user to purge the air bubble from earplug (1020, 1120, 1220). In order to purge an air bubble from earplug (1020, 1120, 1220), the operator may provide additional iontophoresis solution to earplug (1020, 1120, 1220) via conduit (230). The operator may continue to monitor the capacitance value (or some output of system (1000, 1100, 1200) that is based on the capacitance value); and continue delivering additional iontophoresis solution to earplug (1020, 1120, 1220) until the capacitance value increases to a value above the threshold, indicating that the air bubble has been successfully purged. FIG. 23 shows a plot of capacitance over time, illustrating an example of how an air bubble induced drop in capacitance may appear. FIG. 23 also shows how a subsequent increase in capacitance may indicate successful purging of the air bubble.

By way of example only, an operator may deliver additional iontophoresis solution to conduit (230) to purge an air bubble by using a bolus delivery device (430), opening a valve, driving a pump, or otherwise actuating fluid source (140). In continuous feed systems (e.g., such as system (300) described above, etc.), the operator's reaction may entail opening a valve wider, increasing power to a pump, or otherwise increasing the rate of flow of iontophoresis solution to conduit (230). Other suitable forms that an operator's reaction may take will be apparent to those of ordinary skill in the art in view of the teachings herein. Control unit (170) may provide an additional form of audible, visual, and/or haptic feedback to the operator to indicate that the capacitance value has reached a level indicating successful purge of the air bubble.

In addition to or as an alternative to providing feedback to the operator, control unit (170) may automatically drive iontophoresis solution into conduit (230), to thereby automatically purge the air bubble in response to detecting the air bubble. One merely illustrative example of control unit (170) regulating the flow of iontophoresis solution is described in greater detail below; while other examples will be apparent to those of ordinary skill in the art view of the teachings herein. For instance, in non-continuous feed systems, control unit (170) may automatically open a valve, actuate a pump, or otherwise initiate communication of iontophoresis solution to conduit (230) in response to detected drops in capacitance that result from the presence of air bubbles. In continuous feed systems (e.g., such as system (300) described above, etc.), control unit (170) may automatically open a valve wider, increase power to a pump, or otherwise increase the rate of flow of iontophoresis solution to conduit (230) in response to detected drops in capacitance that result from the presence of air bubbles. Other suitable forms that an automated purging response from control unit (170) may take will be apparent to those of ordinary skill in the art in view of the teachings herein. It should also be understood that user feedback may still be provided to the operator (or may be omitted) in versions where control unit (170) provides an automated purging response to detected drops in capacitance that result from the presence of air bubbles.

In some instances, it may be difficult to detect the absolute value of capacitance using electrodes (252, 1002) and interpret that capacitance value to represent whether an air bubble is present, particularly when an air bubble is positioned on the tympanic membrane (TM). In such settings, it may be easier to detect changes in capacitance and interpret those changes to mean that an air bubble is present. If an air bubble is in fact present, its size will fluctuate in response to fluctuating fluid pressure within working channel (221) and the ear canal. This fluctuation in air bubble size will cause fluctuation in the equivalent permittivity of the iontophoresis solution/air bubble combination, which will in turn cause a fluctuation in the sensed capacitance value. In other words, the total equivalent permittivity is a combination of liquid/air permittivity, and since there is a substantial difference between the permittivity of liquid and the permittivity of air, changes in the ratio of the liquid/air bubble volume will change the total equivalent permittivity. Thus, it may be desirable to modulate the fluid pressure of the iontophoresis solution within working channel (221) and the ear canal, to induce fluctuation in the size of any air bubbles in the iontophoresis solution within working channel (221) and the ear canal, such that the resulting changes in capacitance can be detected. If no air bubbles are present, then the sensed capacitance value will not change, even as the fluid pressure is being modulated.

Figure 24:
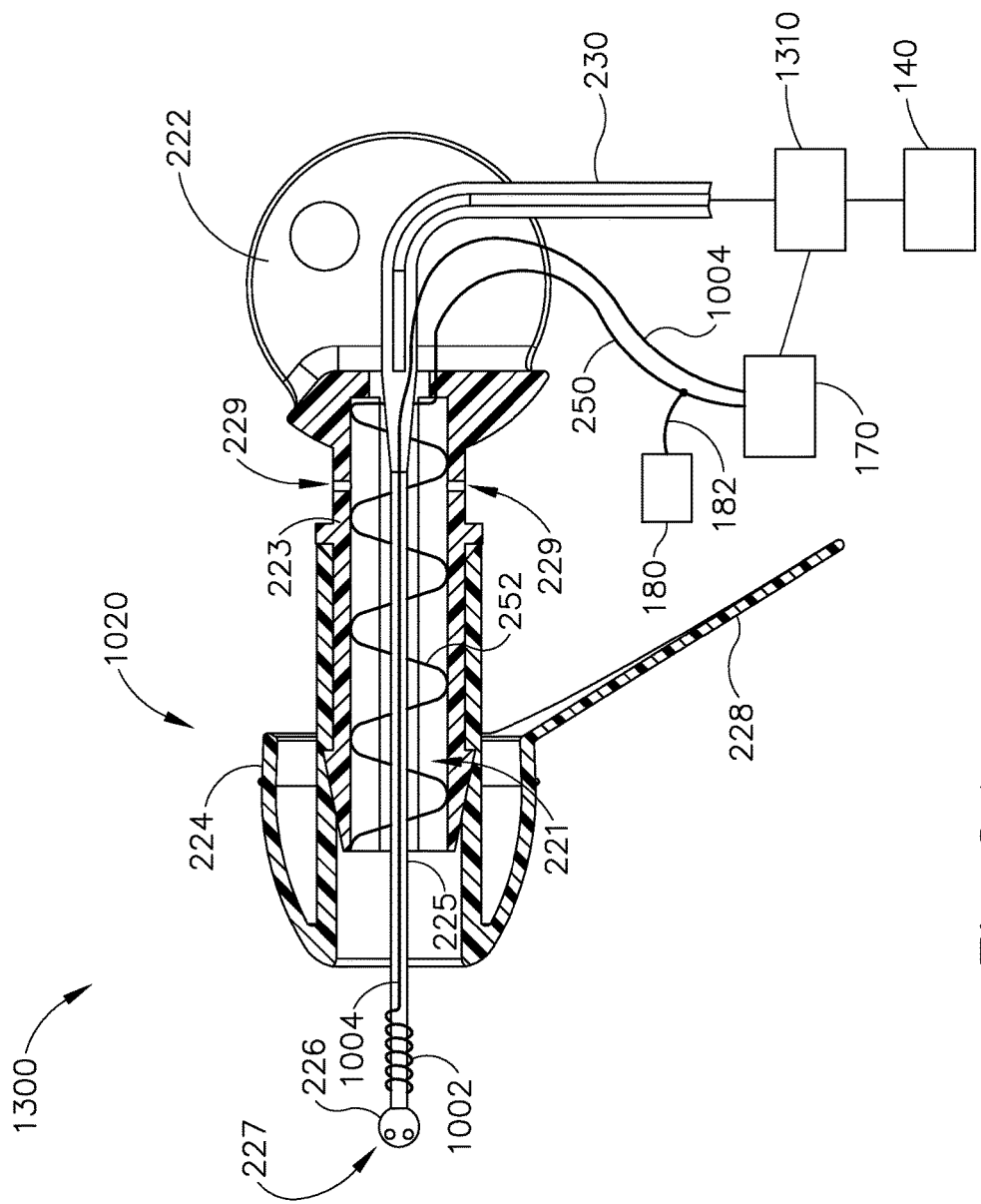
FIG. 24 depicts a side cross-sectional view of yet another exemplary iontophoresis plug with an auxiliary coil for detecting air bubbles around the coil electrode and a iontophoresis solution pressure regulator.

FIG. 24 depicts an exemplary iontophoresis system (1300) that may be used to modulate the fluid pressure of the iontophoresis solution within working channel (221) and the ear canal; and to sense any changes in capacitance resulting from air bubbles. Iontophoresis system (1300) of this example is substantially identical to iontophoresis solution (1000) described above, except that iontophoresis system (1300) of this example includes a pressure modulator (1310) interposed between fluid source (140) and conduit (230). Pressure modulator (1310) is coupled with control unit (170) such that control unit is operable to control pressure modulator (1310). Pressure modulator (1310) is operable to modulate the pressure of fluid communicated to conduit (230), and is thereby operable to modulate the pressure of the iontophoresis solution within working channel (221) and the ear canal. Pressure modulator (1310) may comprise a variable volume reservoir (e.g., bellows, bulb, etc.), a variable flow valve, and/or any other suitable component(s) as will be apparent to those of ordinary skill in the art in view of the teachings herein. Control unit (170) may drive pressure modulator (1310) to modulate the pressure of the iontophoresis solution within working channel (221) and the ear canal as control module (170) monitors changes in capacitance sensed using electrodes (252, 1002). When control module (170) detects an air bubble by detecting a change in the capacitance value, control module (170) may provide any of the responses referred to above. In some versions, control module (170) may actuate pressure modulator (1310) to provide additional iontophoresis solution to conduit (230), to thereby purge an air bubble, in response to detecting the air bubble.

Figure 25:
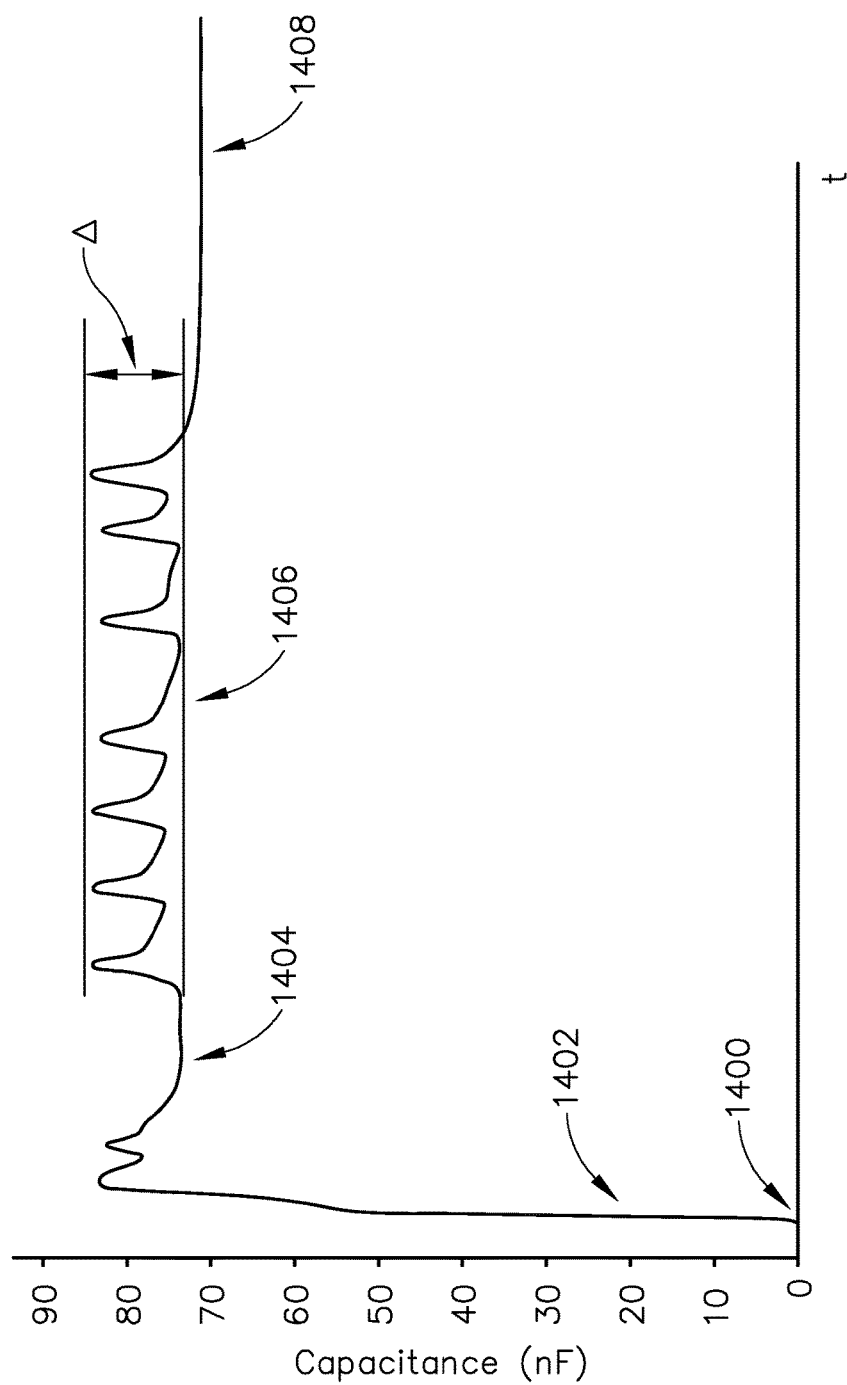
FIG. 25 depicts a signal diagram showing capacitance in the system of FIG. 24 over a period of time.

FIG. 25 shows capacitance over time as sensed using iontophoresis system (1300). At a first period (1400) of time, the capacitance is very low when there is not yet any iontophoresis solution within working channel (221) and the ear canal. At a second period (1402) of time, the capacitance rises as working channel (221) and the ear canal fill with iontophoresis solution. Once working channel (221) and the ear canal are filled with iontophoresis solution, pressure modulator (1310) modulates the pressure of the iontophoresis solution within working channel (221) and the ear canal, resulting in an initial reading of a substantially constant capacitance during a third period (1404) of time. The capacitance starts to change with the modulation of the fluid pressure during a fourth period of time (1406), indicating the presence of an air bubble within working channel (221) and/or the ear canal. The air bubble is purged as described above, resulting in a fifth period (1408) of time where the capacitance value is again substantially constant.

The above-described bubble detection and purging techniques may be implemented in various iontophoresis systems so that the iontophoresis system is always detecting air bubbles, even during iontophoresis. The iontophoresis circuit may be completed by anode electrode (252), the iontophoresis solution, the patient's body, and ground patch (180) attached to the patient's body; while the capacitance measurement circuit may be completed by the anode electrode (252), the iontophoresis solution, and auxiliary electrode (1002). These two systems may work simultaneously by configuring the respective circuits in the control unit (170).

In some other versions, the capacitance sensing circuit is closed for capacitance measurement through ground patch (180), which may eliminate the need for auxiliary electrode (1002). By way of example only, refer back to FIGS. 18-19, which show circuits effectively associated with the combination of earplug (120, 220, 320, 1020, 1120, 1220) and the patient. Some systems may operate on two frequencies to provide sensing of capacitance without an auxiliary electrode (1002), by operating on two frequencies to eliminate the impact of resistance R2 on estimating capacitance C. In the circuit (900) shown in FIG. 18, the impedance of circuit (900) may be calculated as follows:

$$z = \left( R2 + \frac{\frac{R1}{j\omega C}}{R1 + \frac{1}{j\omega C}} \right) = R2 + \frac{R1}{1 + j\omega R1 C} = R2 + \frac{R1 \cdot (1 - j\omega R1 C)}{1 + \omega^2 \cdot R1^2 \cdot C^2} \quad (1)$$

In this equation and others listed herein, $\omega = 2\pi f1$, where f=frequency.

By making the impedance of the circuit (900) shown in FIG. 18 equivalent to the parallel model circuit (950) shown in FIG. 19, the value $C_p$ may be calculated starting with the following formula for impedance of circuit (950):

$$z = \frac{\frac{Rp}{j\omega Cp}}{Rp + \frac{1}{j\omega Cp}} = \frac{Rp}{1 + j\omega Rp Cp} = \frac{Rp(1 - j\omega Rp Cp)}{1 + \omega^2 \cdot Rp^2 \cdot Cp^2} \quad (2)$$

Both the imaginary and the real parts of the impedances for circuits need to be the same in order for the two impedances to be equal, as demonstrated below:

$$\frac{R1^2 \cdot C}{1 + \omega^2 \cdot R1^2 \cdot C^2} = \frac{Rp^2 \cdot Cp}{1 + \omega^2 \cdot Rp^2 \cdot Cp^2} \quad (3)$$

$$R2 + \frac{R1}{1 + \omega^2 \cdot R1^2 \cdot C^2} = \frac{Rp}{1 + \omega^2 \cdot Rp^2 \cdot Cp^2} \quad (4)$$

Thus, the value for $C_p$ may be solved as follows:

$$Cp(R1, R2, C, \omega) := \frac{C \cdot R1^2}{C^2 \cdot R1^2 \cdot R2^2 \cdot \omega^2 + R1^2 + 2 \cdot R1 \cdot R2 + R2^2} \quad (5)$$

The value for $R_p$ may be solved as follows:

$$Rp(R1, R2, C, \omega) := \frac{C^2 \cdot R1^2 \cdot R2^2 \cdot \omega^2 + R1^2 + 2 \cdot R1 \cdot R2 + R2^2}{R2 \cdot C^2 \cdot R1^2 \cdot \omega^2 + R1 + R2} \quad (6)$$

As can be seen from the above, when R2 approaches zero, $C_p$ and the actual capacitance C become the same. For larger values of R2, the measure of $C_p$ is not a good estimate of the actual capacitance C.

Considering two frequencies, f1 and f2, and calculating $C_p$ for these two frequencies using equation (5), the value of actual capacitance C may be calculated based on the values of $C_p$ at those two frequencies per the following formula:

$$C := \frac{f1^2 \cdot Cp1 \cdot (1 + D1^2) - f2^2 \cdot Cp2 \cdot (1 + D2^2)}{f1^2 - f2^2} \quad (7)$$

Where $C_{p1}$ and $C_{p2}$ represent capacitance measured at frequencies of f1 and f2, respectively.

It should therefore be understood that the values $C_p$ and $R_p$ at two different frequencies, f1 and f2, are measured. Then using equation (7), the amount of actual capacitance C is calculated. This value of actual capacitance C is now independent of the value of R2. The magnitude of actual capacitance may be inversely proportional to the size of an air bubble trapped in working channel (221) and/or the ear canal.

By way of example only, above described process may be carried out using a frequency f1 of 100 Hz and a frequency f2 of 120 Hz. These two frequencies may be close enough such that the frequency dependency of the actual capacitance C is negligible. By further optimization of the frequencies f1 and f2, the value of actual capacitance C may be estimated more robustly. As with other air bubble detection processes described herein, the above described process may be carried out at the same time as an iontophoresis process, without interrupting the iontophoresis process. For instance, a DC iontophoresis circuit may be completed by anode electrode (252), the iontophoresis solution, the patient's body, and ground patch (180); while a capacitance measurement circuit may be completed using the same circuit with an AC component. In particular, a small magnitude AC component may be added to the DC component such that the AC component does not interfere with the DC iontophoresis. These two systems may be readily implemented in circuitry of control unit (170). Various suitable ways in which control unit (170) may be configured to provide the dual frequency capacitance sensing described above will be apparent to those of ordinary skill in the art in view of the teachings herein. Similarly, other suitable components, arrangements, and techniques for providing capacitance measurements for air bubble detection will be apparent to those of ordinary skill in view of the teachings herein.

VI. Miscellaneous

It should be understood that any of the examples described herein may include various other features in addition to or in lieu of those described above. By way of example only, any of the devices herein may also include one or more of the various features disclosed in any of the various references that are incorporated by reference herein. It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An iontophoresis apparatus, comprising:
   (a) a first earplug configured for insertion in a first ear of a patient, wherein the first earplug includes:
      (i) a first electrode; and
      (ii) a first fluid port operable to deliver fluid to the first ear;
   (b) a second earplug configured for insertion in a second ear of the patient, wherein the second earplug includes:
      (i) a second electrode; and
      (ii) a second fluid port configured to deliver fluid to the second ear;
   (c) a single ground pad configured to engage exposed skin of the patient and provide an electrical ground return path for the first electrode and the second electrode;
   (d) a driving circuit comprising:
      (i) a first channel configured to receive a first pulsed signal and activate to provide a path for drawing a first current through the first electrode;
      (ii) a second channel configured to receive a second pulsed signal and activate to provide a path for drawing a second current through the second electrode; and
      (iii) a current sink connected to the first and second channels, the current sink configured to alternate between drawing the first current through the first electrode via the first channel and the second current through the second electrode via the second channel; and
   (e) a single control unit configured to couple with the first electrode, the second electrode, and the ground pad, the control unit including a first discharge circuit, a second discharge circuit, a first transistor, and a second transistor, the first discharge circuit being configured to couple to the first electrode downstream from a first transistor, and the second discharge circuit being configured to couple to the second electrode downstream from a second transistor,
   wherein the control unit is configured to:
      provide the first pulsed signal to the first channel and the second pulsed signal to the second channel at alternating clocked intervals;
      alternate between discretely activating the first channel with the first pulsed signal for iontophoretic delivery of the fluid to tissue in the first ear and discretely activating the second channel with the second pulsed signal for iontophoretic delivery of the fluid to tissue in the second ear such that current is drawn through only one of the first electrode and the second electrode at a particular instant and the single ground pad operates as the electrical ground return path.

2. The iontophoresis apparatus of claim 1, wherein the control unit is further configured to provide alternating communication based on the alternating clocked intervals between:
   (i) the first electrode and the current sink; and
   (ii) the second electrode and the current sink.

3. The iontophoresis apparatus of claim 1, wherein the current sink includes an op-amp.

4. The iontophoresis apparatus of claim 3, wherein the current sink further includes a third transistor.

5. The iontophoresis apparatus of claim 4, wherein:
   the op-amp is configured to have an inverting input, a non-inverting input, and an output; and
   the third transistor is configured to couple to the output and provide the inverting input of the op-amp.

6. The iontophoresis apparatus of claim 5, wherein the third transistor is further configured to couple to the first and second channels.

7. The iontophoresis apparatus of claim 1, wherein:
   the first transistor is configured to couple with the first electrode and receive the first pulsed signal and activate the first channel; and
   the second transistor is configured to couple with the second electrode and receive the second pulsed signal and activate the second channel.

8. The iontophoresis apparatus of claim 7, wherein the first pulsed signal and the second pulsed signal are 180 degrees out of phase with each other.

9. The iontophoresis apparatus of claim 7, wherein:
   the first discharge circuit is configured to receive a first input signal and discharge built-up charge across tissue in the first ear from the first electrode; and
   the second discharge circuit is configured to receive a second input signal and discharge built-up charge across tissue in the second ear from the second electrode.

10. The iontophoresis apparatus of claim 1, wherein the first discharge circuit includes a fourth transistor configured to receive the first input signal and switch on, and wherein the second discharge circuit includes a fifth transistor configured to receive the second input signal and switch on.

11. The iontophoresis apparatus of claim 10, wherein the first discharge transistor is configured to provide a first discharge path for the built-up charge across tissue in the first ear when the first discharge transistor is switched on, wherein the second discharge transistor is configured to provide a second discharge path for the built-up charge across tissue in the second ear when the second discharge transistor is switched on.

12. The iontophoresis apparatus of claim 11, wherein the first and second input signals are 180 degrees out of phase with each other.

13. The iontophoresis apparatus of claim 11, wherein the control unit is configured to:
   provide the first current through the first electrode while the second discharge transistor receives the second input signal; and
   provide the second current through the second electrode while the first discharge transistor receives the first input signal.

14. The iontophoresis apparatus of claim 13, wherein the control unit is further configured to:
   stop the first current through the first electrode when the first discharge transistor receives the first input signal; and
   stop the second current through the second electrode when the second discharge transistor receives the second input signal.

15. The iontophoresis apparatus of claim 1, wherein current drawn through the first and second electrodes is a modulated AC current.

16. The iontophoresis apparatus of claim 8, wherein the first pulsed signal and the second pulsed signal have a common frequency that is configured to provide substantially simultaneous activation of the first electrode and the second electrode.

17. The iontophoresis apparatus of claim 12, wherein the first input signal is the second pulsed signal and the second input signal is the first pulsed signal.

18. The iontophoresis apparatus of claim 1, wherein the control unit is further configured to regulate iontophoretic delivery to the first and second ears by monitoring current drawn through the first and second electrodes.

19. The iontophoresis apparatus of claim 1, wherein the first discharge circuit is configured to discharge a charge remaining in the first electrode after the first current is drawn through the first electrode and the second discharge circuit is configured to discharge a charge remaining in the second electrode after the second current is drawn through the second electrode.

20. An iontophoresis apparatus, comprising:
(a) a first earplug configured for insertion in a first ear of a patient, wherein the first earplug includes:
  (i) a first electrode; and
  (ii) a first fluid port operable to deliver fluid to the first ear;
(b) a second earplug configured for insertion in second ear of the patient, wherein the second earplug includes:
  (i) a second electrode; and
  (ii) a second fluid port configured to deliver fluid to the second ear;
(c) a single ground pad configured to engage exposed skin of the patient and provide an electrical ground return path for the first electrode and the second electrode;
(d) a driving circuit comprising:
  (i) a first channel configured to receive a first pulsed signal and activate to provide a path for drawing a first current through the first electrode;
  (ii) a second channel configured to receive a second pulsed signal and activate to provide a path for drawing a second current through the second electrode; and
  (iii) a current sink connected to the first and second channels, the current sink configured to alternate between drawing the first current through the first electrode via the first channel and the second current through the second electrode via the second channel; and
(e) a single control unit configured to couple with the first electrode, the second electrode, and the ground pad, the control unit including:
  (i) a first transistor configured to couple with the first electrode, the first transistor configured to receive the first pulsed signal and activate the first channel;
  (ii) a second transistor configured to couple with the second electrode, the second transistor configured to receive the second pulsed signal and activate the second channel,
  (iii) a first discharge circuit configured to couple with the first electrode, the first discharge circuit being configured to receive a first input signal and discharge built-up charge across tissue in the first ear from the first electrode; and
  (iv) a second discharge circuit configured to couple with the second electrode, the second discharge circuit being configured to receive a second input signal and discharge built-up charge across tissue in the second ear from the second electrode, the first discharge circuit including a first discharge transistor configured to receive the first input signal and switch on, the second discharge circuit including a second discharge transistor configured to receive the second input signal and switch on, the control unit being configured to:
provide the first pulsed signal to the first channel and the second pulsed signal to the second channel at alternating clocked intervals;
alternate between discretely activating the first channel with the first pulsed signal for iontophoretic delivery of the fluid to tissue in the first ear and discretely activating the second channel with the second pulsed signal for iontophoretic delivery of the fluid to tissue in the second ear such that current is drawn through only one of the first electrode and the second electrode at a particular instant and the single ground pad operates as the electrical ground return path.

* * * * *